(12) United States Patent
Katukuri et al.

(10) Patent No.: US 8,494,987 B2
(45) Date of Patent: Jul. 23, 2013

(54) SEMANTIC RELATIONSHIP EXTRACTION, TEXT CATEGORIZATION AND HYPOTHESIS GENERATION

(75) Inventors: Jayasimhaa Reddy Katukuri, Lafayette, LA (US); Vijay Varadachari Raghavan, Lafayette, LA (US); Ying Xie, Kennesaw, GA (US)

(73) Assignee: Araicom Research LLC, Baton Rouge, LA (US)

( * ) Notice: Subject to any disclaimer, the term of this patent is extended or adjusted under 35 U.S.C. 154(b) by 886 days.

(21) Appl. No.: 12/361,433

(22) Filed: Jan. 28, 2009

(65) Prior Publication Data

US 2009/0192954 A1    Jul. 30, 2009

Related U.S. Application Data

(63) Continuation-in-part of application No. PCT/US2007/063983, filed on Mar. 14, 2007, which is a continuation-in-part of application No. 12/210,253, filed on Sep. 15, 2008.

(60) Provisional application No. 61/024,099, filed on Feb. 28, 2008, provisional application No. 60/782,935, filed on Mar. 15, 2006.

(51) Int. Cl.
*G06N 5/00* (2006.01)

(52) U.S. Cl.
USPC ............................................ 706/13; 706/45

(58) Field of Classification Search
USPC .................................................... 706/11, 45
See application file for complete search history.

(56) References Cited

U.S. PATENT DOCUMENTS

| | | | |
|---|---|---|---|
| 4,942,526 | A | 7/1990 | Okajima et al. |
| 5,499,340 | A | 3/1996 | Barritz |
| 6,233,609 | B1 | 5/2001 | Mittal |
| 7,657,424 | B2 | 2/2010 | Bennett |
| 2002/0129031 | A1 | 9/2002 | Lau et al. |
| 2004/0010483 | A1 | 1/2004 | Brands et al. |
| 2004/0015464 | A1 | 1/2004 | Li et al. |
| 2007/0083359 | A1 | 4/2007 | Bender |

FOREIGN PATENT DOCUMENTS

| | | |
|---|---|---|
| WO | WO 2007/106858 A2 | 9/2007 |
| WO | WO 2008/134279 A1 | 11/2008 |

OTHER PUBLICATIONS

Hofmann, et al., Concept-based annotation of enzyme classes, Bioinformatics, Department of Biochemistry, University of Cologne, Germany, Jan. 18, 2005, pp. 2059-2066.*

Bouskila, The Role of Semantic Locality in Hierarchical Distributed Dynamic Dynamic Indexing and Information Retrieval, Master's Thesis, Graduate College of the University of Illinois at UrbanaChampaign, 1999, pp. 1-93.*

(Continued)

*Primary Examiner* — Wilbert L Starks
(74) *Attorney, Agent, or Firm* — Alston & Bird LLP

(57) ABSTRACT

Embodiments of the present invention are generally related to systems, methods, computer readable media, and other means for extracting entities, determining the semantic relationships among the entities and generating knowledge. More particularly, some embodiments of the present invention are directed to generating a hypothesis and/or gaining knowledge by automatically extracting semantic relationships from electronic documents stored at remote databases, which are accessed over the Internet. Some embodiments of the present invention also include textual categorization and new approaches and algorithms for solving the problems of relationship extraction, computing semantic relationships and generating hypotheses.

19 Claims, 9 Drawing Sheets

OTHER PUBLICATIONS

Hristovski, et al., Using literature-based discovery to identify disease candidate genes, International Journal of Medical Informatics (2005) 74, pp. 289-298.*

Cristianini et al., *An Introduction to Support Vector Machines and Other Kernel Based Learning Algorithms*, Cambridge University Press (2000) (Abstract Only).

Joachims, *Learning to Classify Text Using Support Vector Machines: Methods, Theory and Algorithms*, Kluwer Academic Publisher (2002) (Abstract Only).

Sullivan, *Document Warehouse and Text Mining*, John Wiley & Sons (2001) (Abstract Only).

*Arrowsmith Project: Linking Documents, Disciplines, Investigators, and Databases* (Homepage), University of Illinois at Chicago, last modified Dec. 20, 2007. http://arrowsmith.psych.uic.edu/arrowsmith_uic/index.html.

Bekhuis, *Conceptual Biology, Hypothesis Discovery, and Text Mining*: Swanson's legacy, Biomedical Digital Libraries, Apr. 3, 2006; 7 pages; BioMed Central.

Blagosklonny et al., *Unearthing the Gems*, Nature, Mar. 28, 2002; p. 373; vol. 416; Macmillan Magazines Ltd.

Blaschke et al., *The Frame-Based Module of the SUISEKI Information Extraction System*, IEEE Intelligent Systems, 2002; pp. 14-20.

Bunescu et al., *Subsequence Kernels for Relation Extraction*, Proceedings of the 19th Conference on Neural Information Processing Systems; 2005; pp. 171-178.

Califf et al., *Bottom-Up Relational Learning of Pattern Matching Rules for Information Extraction*, Journal of Machine Learning Research, Jun. 2003; pp. 177-210.

Cancedda et al., *Word-Sequence Kernels*, Journal of Machine Learning Research, Feb. 2003; pp. 1059-1082.

Chang et al., *Extracting and Characterizing Gene-drug Relationships From the Literature*, Pharmacogenetics, Sep. 2004; pp. 577-586; vol. 14, No. 9; Lippincott Williams & Wilkins.

Cheng et al., *Discriminative Frequent Pattern Analysis for Effective Classification*, IEEE, 2007; pp. 716-725.

Cohen et al., *A Survey of Current Work in Biomedical Text Mining*, Briefings in Bioinformatics, Mar. 2005; pp. 57-71; vol. 6, No. 1; Henry Stewart Publications.

Collins et al., *Convolution Kernels for Natural Language*, Proceedings of Neural Information Processing Systems; 2001; 8 pages.

Gaizauskas, *An Information Extraction Perspective on Text Mining: Tasks, Technologies and Prototype Applications*; Euromap Text Mining Seminar; Sep. 4, 2002.

Goadrich et al., *Learning Ensembles of First-Order Clauses for Recall-Precision Curves: A Case Study in Biomedical Information Extraction*; ILP 2004, LNAI 3194, pp. 98-115.

Gordon et al., *Toward Discovery Support Systems: A Replication, Re-Examination, and Extension of Swanson's Work on Literature-Based Discovery of a Connection between Raynaud's and Fish Oil*, Journal of the American Society for Information Science, Feb. 1996; pp. 116-128.

Grishman, *Information Extraction: Techniques and Challenges*, International Summer School on Information Extraction: A Multidisciplinary Approach to an Emerging Information Technology; pp. 10-27; 1997; vol. 1299; Springer-Verlag, London, UK.

Hearst, *Untangling Text Data Mining*, Proceedings of the 37th Annual Meeting of the Association for Computational Linguistics on Computational Linguistics; 1999; pp. 3-10; Association for Computational Linguistics, Morristown, NJ.

Hu et al., *Mining Hidden Connections among Biomedical Concepts from Disjoint Biomedical Literature Sets through Semantic-Based Association Rule*, Journal of Information Systems; Jun. 2006, 20 pages; Association for Information Technology Professionals—Special Interest Group for Education.

International Search Report for PCT/US2007/063983, mailed Jul. 12, 2007.

International Search Report for PCT/US2008/060984, mailed Jul. 2, 2008.

Jensen et al., *Literature Mining for the Biologist: From Information Retrieval to Biological Discovery*, Nature Reviews/Genetics; Feb. 2006; pp. 119-129; vol. 7; Nature Publishing Group.

Kamvar et al., *Inducing Novel Gene-Drug Interactions from the Biomedical Literature*, Bioinformatics, 2003; pp. 1-8; vol. 1, No. 1; Oxford Press.

Lodhi et al., *Text Classification Using String Kernels*;Journal of Machine Learning Research; Feb. 2002; pp. 419-444.

Moreno et al., *A Kullbck-Leibler Divergence Based Kernel for SVM Classification in Multimedia Applications*, Jan. 2004; 9 pages; Hewlett-Packard Company.

Perez-Iratxeta et al., *Association of Genes to Genetically Inherited Diseases Using Data Mining*, Nature Genetics, Jul. 2002, pp. 316-319, vol. 31.

Perez-Iratxeta, et al.; *G2D: A Tool for Mining Genes Associated With Disease*, BMC Genetics, vol. 6, No. 45 (2005).

Pratt et al., *LitLinker: Capturing Connections across the Biomedical Literature*: Proceedings of the 2nd International Conference on Knowledge Capture; 2003; pp. 105-112; Association for Computer Machinery, New York, NY.

Ray et al., *Representing Sentence Structure in Hidden Markov Models for Information Extraction*, Proceedings of the 17th International Joint Conference on Artificial Intelligence; 2001; 7 pages.

Rosario, et al., *Classifying Semantic Relations in Bioscene Texts*, Proceedings of the 42nd Annual Meeting on Association for Computational Linguistics; 2004; Article No. 430, 8 pages; Association for Computational Linguistics, Morristown, NJ.

Rosario, et al., *Multi-way Relation Classification: Application to Protein-Protein Interactions*, Proceedings of the Conference on Human Language Technology and Empirical Methods in Natural Language Processing; 2005; pp. 732-739; Association for Computational Linguistics, Morristown, NJ.

Schuemie et al., *Distribution of Inormation in Biomedical Abstracts and full-text Publications*, Bioinformatics, May 6, 2004; pp. 2597-2604; vol. 20. Issue 16; Oxford University Press.

Settles et al., *ABNER: An Open Source Tool for Automatically Tagging Genes, Proteins and Other Entity Names in Text*, Applications Note, Apr. 28, 2005; pp. 3191-3192, vol. 21, No. 14.

Shah et al., *Information Extraction From Full Text Scientific Articles: Where are the Keywords?*; BMC Bioinformatics, May 2003; 9 pages; BioMed Central.

Smalheiser et al., *"Using ARROWSMITH: A Computer-assisted Approach to Formulating and Assessing Scientific Hypotheses,"* Computer Methods and Programs in Biomedicine 1998; 57: 149-153.

Smalheiser, *"The Arrowsmith Project: 2005 Status Report,"* A. Hoffmann, H. Motoda, and T. Scheffer (Eds.): DS 2005, LNAI 3735, pp. 26-43 (2005).

Srinivasan, *Text Mining: Generating Hypotheses From MEDLINE*, Journal of the American Society for Information Science and Technology, 2004; pp. 396-413.

Stegmann et al., *Hypothesis Generation Guided by co-word Clustering*, Scientometrics, 2003, pp. 111-135, vol. 56, No. 1, Akadémiai Kiadó, Budapest, and Kluwer Academic Publishers, Dordrecht.

Swanson, *Fish Oil, Raynaud's Syndrome, and Undiscovered Public Knowledge*; Perspectives in Biology and Medicine, Division of the Biological Sciences, The University of Chicago; 1986, pp. 7-18; The University of Chicago.

Swanson, *Medical Literature as a Potential Source of New Knowledge*, Bull Med. Libr. Assoc. 78(1), Jan. 1990; pp. 29-37.

Swanson, *Somatodedin C and Arginine: Implicit Connections Between Mutually Isolated Literatures*, Perspectives in Biology and Medicine, Winter 1990; pp. 157-186; vol. 33, No. 2, Division of the Biological Sciences, The University of Chicago.

Takeuchi et al., *Bio-Medical Entity Extraction using Support Vector Machines*, Proceedings of the ACL 2003 Workshop on Natural Language Processing in Biomedicine; 2003; pp. 57-64; ; vol. 13; Association for Computational Linguistics, Morristown, NJ.

Thomas et al., *Automatic Extraction of Protein Interactions from Scientific Abstracts*, Pacific Symposium on Biocomputing; 2000; 12 pages.

Wallach, *Conditional Random Fields: An Introduction*, University of Pennsylvania CIS Technical Report; MS-CIS-04-21, Feb. 24, 2004; 9 pages.

Weeber et al, *Text-based Discovery in Biomedicine: the Architecture of the DAD-system*, Proceedings of the AMIA Annual FALL Symposium, Hanley and Belfus, Philadelphia, 2000, pp. 903-907.

Weeber et al., *Using Concepts in Literature-Based Discovery: Simulating Swanson's Raynaud-Fish Oil and Migraine-Magnesium Discoveries*, Journal of the American Society for Information Science and Technology, Wiley & Sons: New York, NY, vol. 52, No. 7, May 1, 2001, pp. 548-569.

Weeber et al., *Generating Hypotheses by Discovering Implicit Associations in the Literature: A Case Report of a Search for New Potential Therapeutic Uses for Thalidomide*, Journal of the American Medical Informatics Association [Online], vol. 10, No. 3, May 2003, pp. 252-259.

Xie et al., *Conceptual Biology Research Supporting Platform: Current Design and Future Directions*, Studies in Computational Intelligence (SCI); 2008; pp. 307-324; 122; Springer-Verlag Berlin Heidelberg.

Xie et al., *Language-Modeling Kernel Based Approach for Information Retrieval*, Journal of the American Society for Information Science and Technology; 2007; pp. 2353-2365; 58(14); Wiley Periodicals, Inc.

Yang et al., *A Comparative Study on Feature Selection in Text Categorization*, Proceedings of the Fourteenth International Conference on Machine Learning; 1997; pp. 412-420; Morgan Kaufmann Publishers, Inc., San Francisco, CA.

Zelenko et al., *Kernel Methods for Relation Extraction*, Journal of Machine Learning Research, , Feb. 2003; pp. 1083-1106.

Aronson et al. "Query Expansion Using the UMLS Metathesaurus,", *AMIA, Inc.*, pp. 485-489. (1997).

Cimino et al. "Automatic knowledge acquisition from MEDLINE", *Methods of Information in Medicine*, 32:120-130, (1993).

Cohen et al. "Using co-occurrence network structure to extract synonymous gene and protein names from MEDLINE abstract," *BMC Bioinformatics*, 15 pages, (2005).

Elkin et al., "Mapping to MeSH, (The Art of Trapping MeSH Equivalence from within Narrative Text)," *SCAMC, Inc.*, pp. 185-190, (1998).

Hersh et al. "SAPHIRE—An information retrieval system featuring concept matching, automatic indexing, probabilistic retrieval, and hierarchical relationships," *Computers and Biomedical Research*, 23:410-425, (1990).

Rindflesch et al. "Ambiguity resolution while mapping free text to the UMLS metathesaurus," *AMIA, Inc.*, pp. 240-244, (1994).

Srinivasan "Optimal Document-Indexing Vocabulary for MEDLINE," *Information Processing & Management*, 32(5):503-514. (1996).

Srinivasan, "Retrieval feedback for query design in MEDLINE. A comparison with expert network and LLSF approaches," *AMIA, Inc.*, pp. 353-357, (1996).

Sullivan, "What is Text Mining?," *Document Warehousing and Text Mining*, Chapter 13, Wiley Computer Publishing, pp. 323-368, (2001).

* cited by examiner

SEMANTIC RELATIONSHIP EXTRACTION, TEXT CATEGORIZATION AND HYPOTHESIS GENERATION

CROSS-REFERENCE TO RELATED APPLICATIONS

This patent application claims priority from U.S. Provisional Patent Application No. 61/024,099, filed Jan. 28, 2008, titled "Method and System for Relationship Extraction and Enhancement of Hypothesis Discovery," and is a Continuation-in-Part of U.S. patent application Ser. No. 12/210,253, filed Sep. 15, 2008, which was a continuation and claims the benefit of International Patent Application PCT/US2007/063983, filed Mar. 14, 2007, which claims the benefit of U.S. Provisional Patent Application No. 60/782,935, filed Mar. 15, 2006, each of which is incorporated herein by reference in its entirety.

FIELD OF THE INVENTION

Many embodiments of the present invention are generally related to systems, methods, computer readable media, and other means for parsing information and generating knowledge. More particularly, some embodiments of the present invention are directed to generating a hypothesis and/or gaining knowledge by automatically extracting semantic relationships from information stored as electronic data. Some embodiments of the present invention also include textual categorization and new approaches to the problem of relationship extraction between textual entities derived from, for example, biomedical literature.

BACKGROUND

As modern society evolves, more and more textual information is being stored as electronic data. The textual information can be derived from electronic copies of scientific articles, patents, web pages, electronic books, among others. Textual information can also be included in graphics or metadata associated with images and videos.

Accordingly, the amount of textual electronic data continues to grow. Some say the growth is exponential. For example, MEDLINE, which is a database of medical publications from more than 4600 journals, currently has more than a total of 16 million documents. Literature is an important source of knowledge and, in certain fields (such as medicine), it is the only comprehensive source. In the field of molecular biology, for example, protein interactions play a significant role. The evidence for a majority of protein interactions is present only in the literature. On the one hand, literature is an important part of research for biomedical researchers, and on the other hand, the researchers are overwhelmed with the number of documents being published. This rapid growth of data, while being overwhelmingly encouraging for researchers, creates a number of new problems. For example, large quantities of data can be hard for any group of people to sort and classify, let alone one person read and understand. In other words, it is becoming ever more difficult for any one person or even groups of people to keep abreast of all the developments in a just a single field or with respect to a particular subject matter or event.

There are currently many systems and methods available that facilitate the capture and creation of this data. The data is often then stored in a database structure or a spreadsheet, which are collectively referred to herein as databases or information sources regardless of the type, system, or structure.

The data stored in databases can be formatted in a variety of ways, including the XML format.

In addition, people commonly use other systems specifically designed to search for and retrieve data from the databases. These searching systems are often referred to as search engines. Some well known examples of search engines include Google® of Google Corporation of Mountain View, Calif., Baidu® of Baidu.com Corporation of Beijing, China, Yahoo!® and AltaVista® of Yahoo! Corporation of Sunnyvale, Calif., MSN® and Windows Live® of Microsoft Corporation of Redmond, Wash.

More recently, researchers have begun focusing their attention on other types of systems, called information extraction systems. Such systems and methods involve the extraction of information from natural language text. Information, as referenced in these systems, is comprised of entities and relationships between the entities. For the information extraction systems to operate, the systems must have access to information in a compatible electronic format. Web pages and other electronic documents are examples of where electronic versions of such information can be found today. For example, the website www.Pubmed.gov can be used to access a database of electronic medical information. As another example, commonly-assigned, International Application No. PCT/US08/60984, filed Apr. 21, 2008, discusses how to infer information and profile knowledge based on the associative relevancy of information to other information. Accordingly, International Application No. PCT/US08/60984 is incorporated by reference herein in its entirety, especially the portions regarding inferring information and knowledge profiling architectures that permit the capture and use of associations between known reference sets.

In many instances, information extraction can be generally described as ways of creating a structured database from natural language text documents, so that traditional knowledge discovery and data mining techniques can be efficiently applied. Accordingly, information extraction is complicated by the fact that natural languages are flexible, and words can take on different meanings depending upon their context (i.e., how the words are used in a sentence, paragraph and/or document). This problem is further compounded by the fact that the same thing can be said in different ways.

Some information extraction systems require a user to provide an initiating concept (concept "A"). This system is sometimes referred to as an open discovery system. An open discovery system retrieves the document set previously categorized by a user (i.e., manually) as being related to concept A, by querying a database (such as the one accessed via, e.g., www.Pubmed.gov). The open discovery system then tries to compute the set of frequently occurring concepts (concepts B) from the document set, and then retrieves the document set for each of the frequent B terms by querying the database to compute the set of C terms. One limitation to the open discovery system is a lack of scalability if a user is interested in hypotheses related a broad category, like "Disease or Syndrome," or a large group of users exist, because such instances require sending several hundreds of queries for each initiating concept. Another, more apparent limitation is that the set of hypotheses generated by the system are limited to only the initiating concepts A by a group of users. In other words, an open system may omit some interesting hypotheses, because it does not have one of the initiating concepts.

BRIEF SUMMARY

Many embodiments of the present invention are generally related to systems, methods, computer readable media, and other means for parsing information and generating knowledge. More particularly, some embodiments of the present invention are directed to generating a hypothesis and/or gaining knowledge by automatically extracting semantic relationships from information stored as electronic data. Some embodiments of the present invention also include textual categorization and new approaches to the problem of relationship extraction between textual entities derived from, for example, biomedical literature.

For example, some embodiments of the present invention involve a hypothesis generation system, methods and computer program product comprising a computer-readable storage medium having computer-readable program code. The hypothesis generation system can include a number of different modules and engines, which may be located within a single apparatus or distributed among a number of machines.

One such module is a communications module. The communications module can be configured to communicate with, among other things, a remote database. In addition, the communications module can be configured to help facilitate the downloading of data from the remote database.

The hypothesis generation engine can be configured to execute various processes and algorithms to generate a hypothesis based on co-occurring concepts among textual documents. The co-occurring concepts are usually extracted using one or more different types of entity extracting and semantic extracting algorithms and processes. The entity extracting and semantic extracting can be performed by dedicated modules or engines (such as those discussed herein).

The hypothesis generation engine can also be configured to pre-compute co-occurring concepts included in the data, wherein the pre-computing occurs prior to receiving a command to generate a hypothesis. The co-occurring concepts can be stored, for example, while waiting for the command to generate a hypothesis. The computing of the co-occurring concepts can take place in response to a user interaction with the system, a preconfigured setting, an automatic, periodic update request (e.g., every week, every year, every day, etc.), and/or in response to any other input or trigger means.

The command to generate a hypothesis can be generated in response to, for example, a user interaction with the system. Once the hypothesis generation command is received (from an input component, communications component, or central processor), the hypothesis generation engine can generate a hypothesis based on the co-occurring concepts that were previously computed and extracted. The hypothesis can then be transformed into results that are user-comprehendible information that can be presented on a display screen.

As used herein, the terms "data" and "information" are used independently. Information refers to content that an average person understands (as opposed to one skilled in the electrical and computer arts), while data refers to the representation of information or knowledge stored in the form of the bits a machine uses. For example, a person can read textual information that is derived from and corresponds with text data stored on a computer's storage component and displayed by a computer's display screen. Information can be visual, audible, and/or tactile. Data can be formatted in any suitable manner and can include electrical, optical, or any other type of signal, The separate terms data and information are generally used independently to be more descriptive of various types of content and also to distinguish the content of data and information from "knowledge."

As used herein, the term "knowledge" refers to a higher order of information, or context in which to interpret information, that imparts an awareness or comprehension of a subject matter domain by a specialized user (referred to herein as a domain expert), and is inclusive of at least one association between two known reference sets, also referred to as associative knowledge. Knowledge, as used herein, is not merely some additional piece of data or information, but is a special form of information that is generated by a domain expert, or by like function, through awareness and comprehension of a domain. Knowledge may be found in many forms, but is often nonfunctional, such as embedded in the form in which it is found. For example, literature and other forms of documents written by an expert, typically contain some representation of knowledge as the writing is typically created with the subjective interpretation of the expert. But, as embedded in the literature, the knowledge becomes inherent to part of the information and is nonfunctional.

BRIEF DESCRIPTION OF THE DRAWINGS

Figure 1:
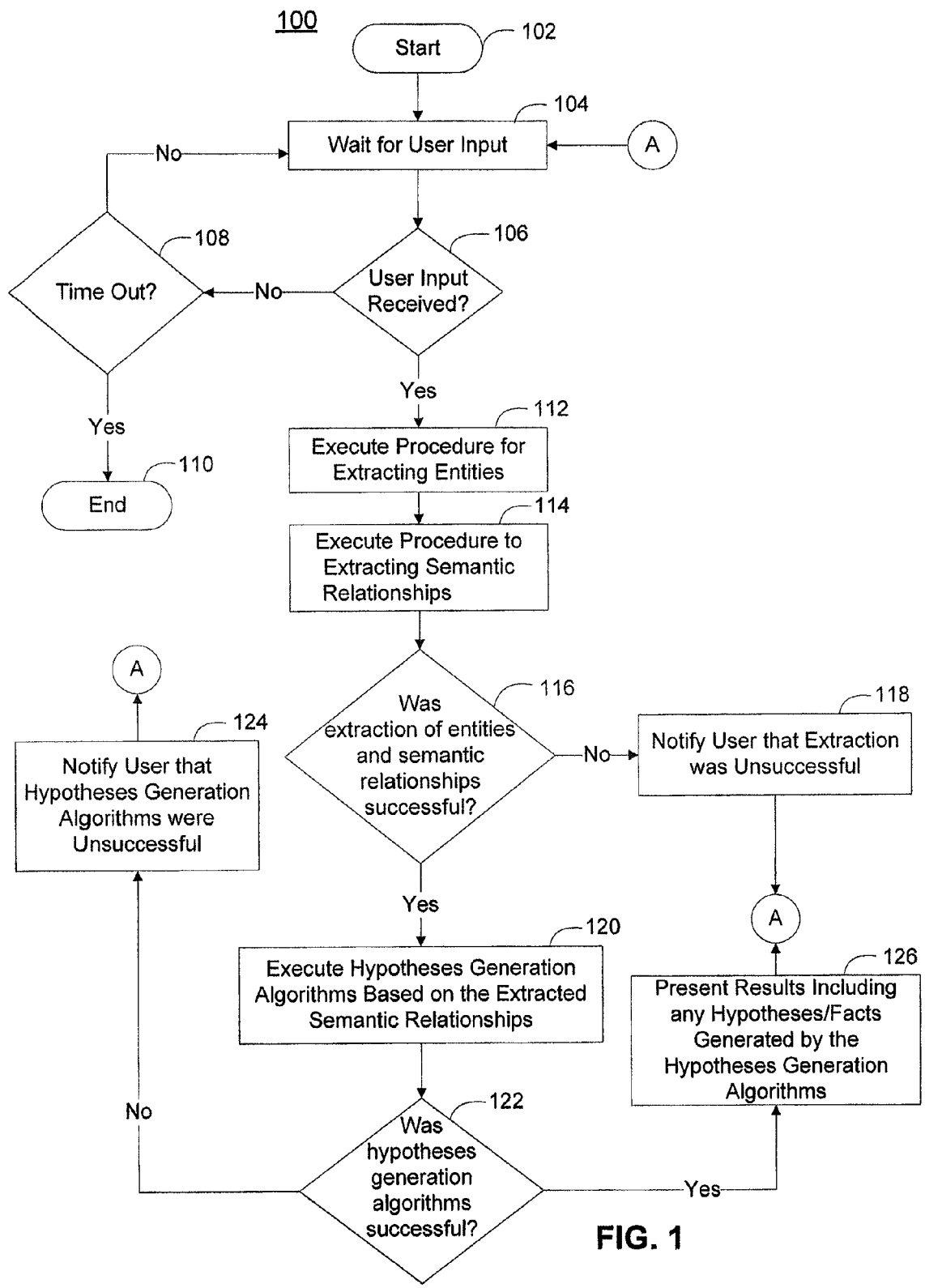
Figure 2:
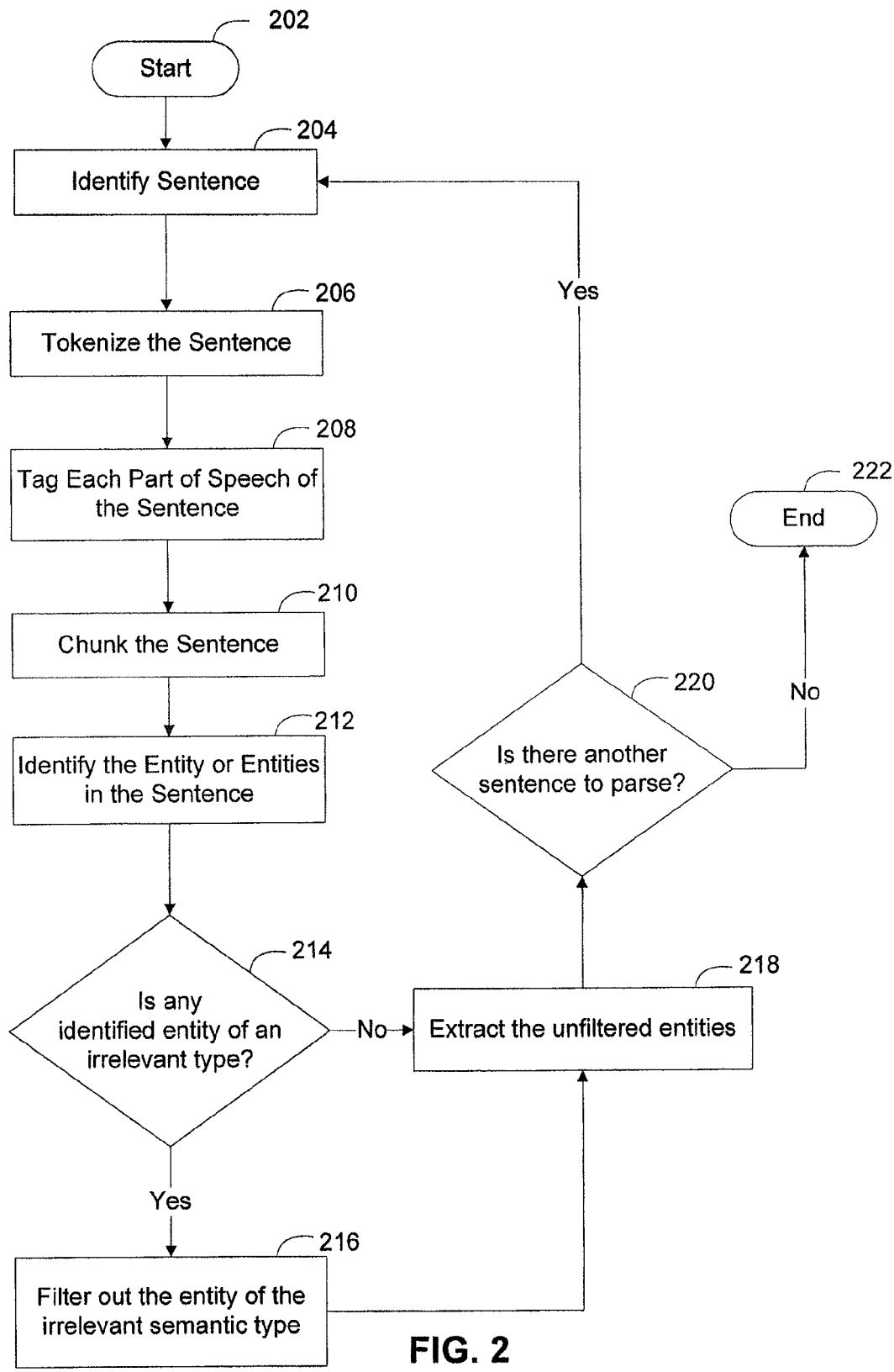
Figure 3:
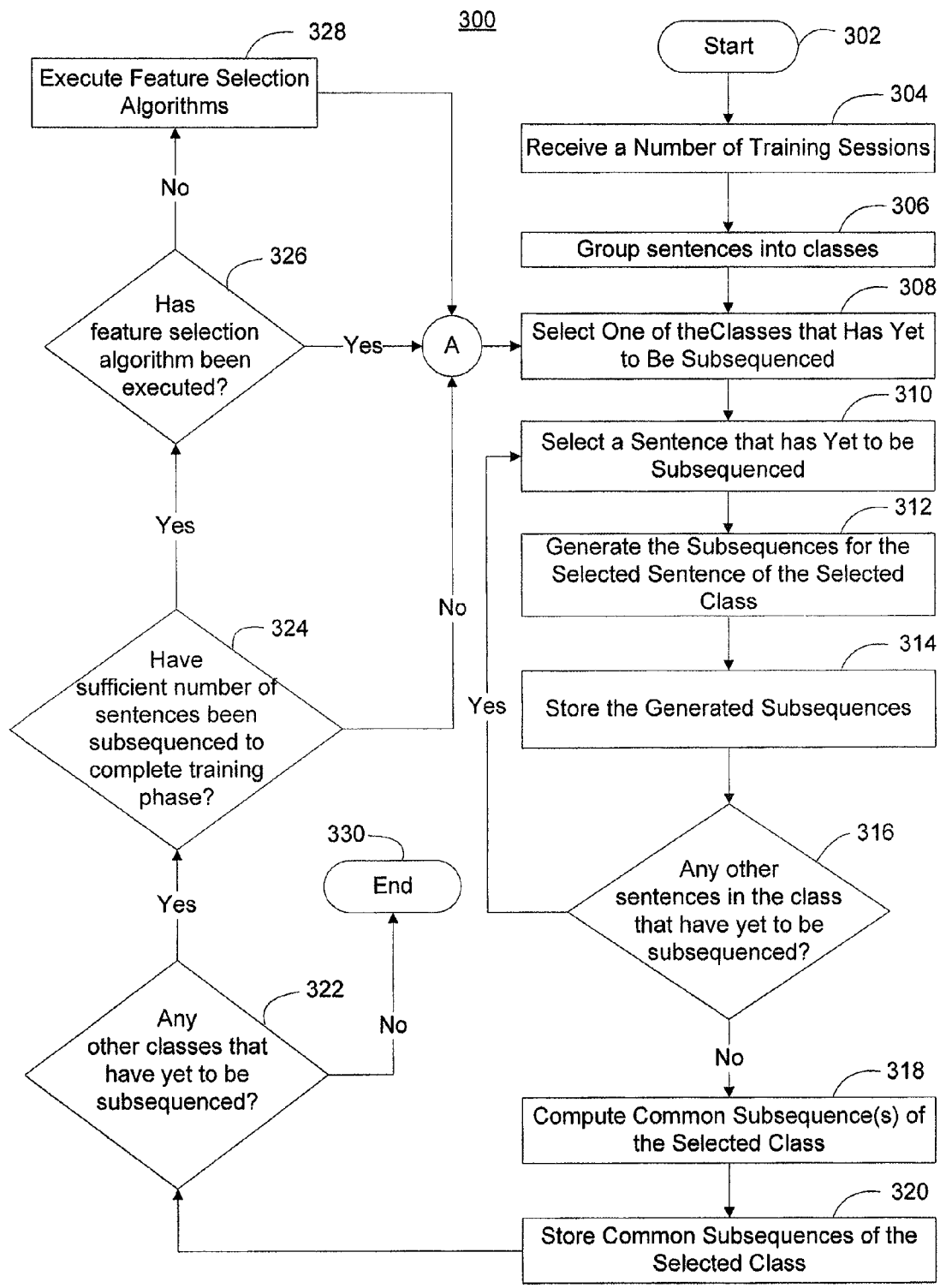
Figure 4:
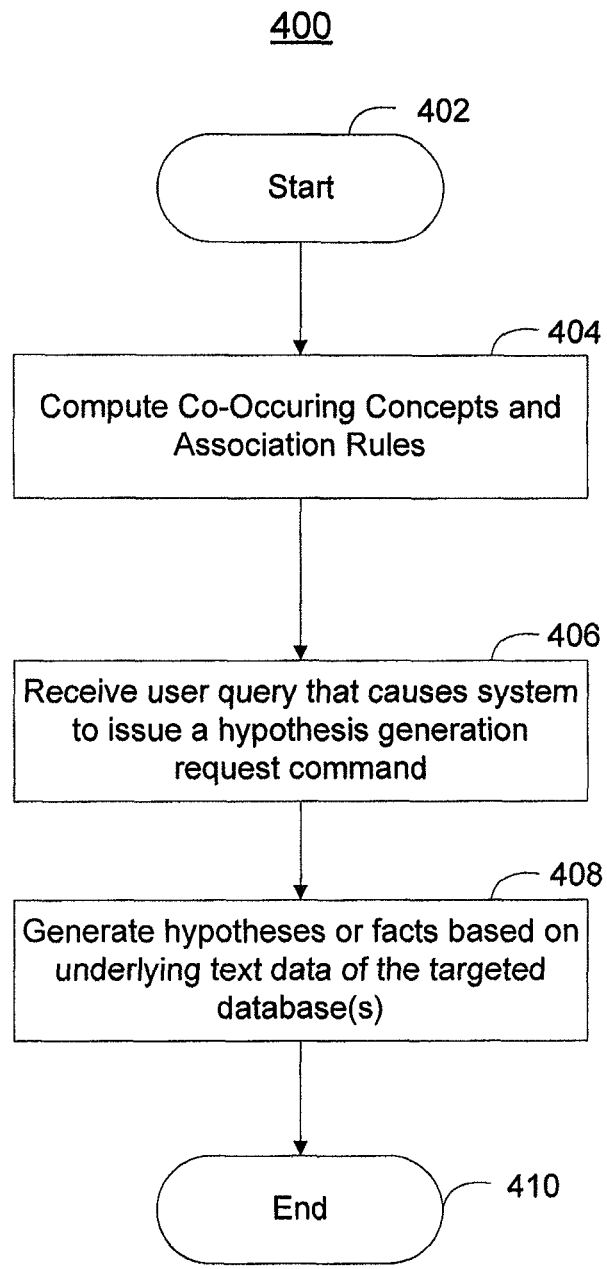
Figure 9:
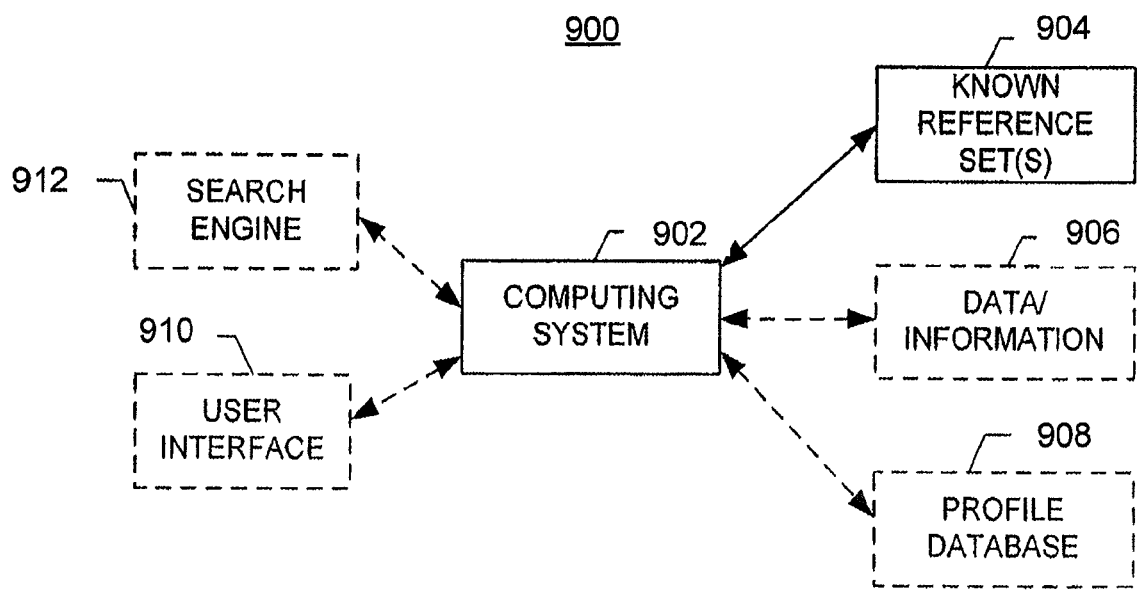
Figure 10:
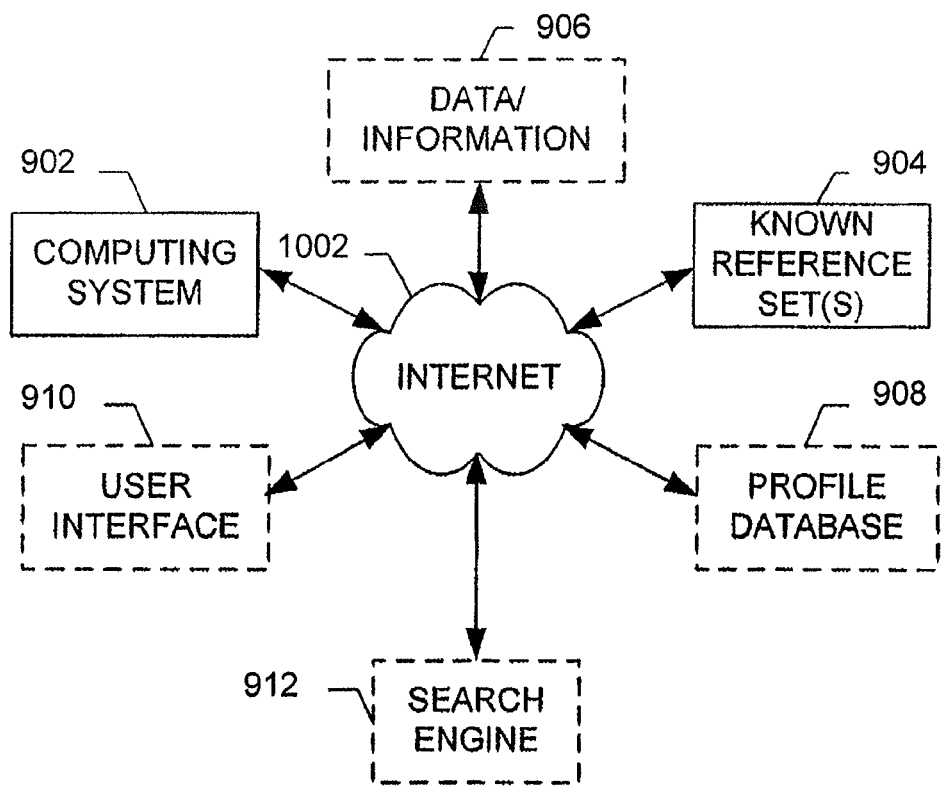
Figure 11:
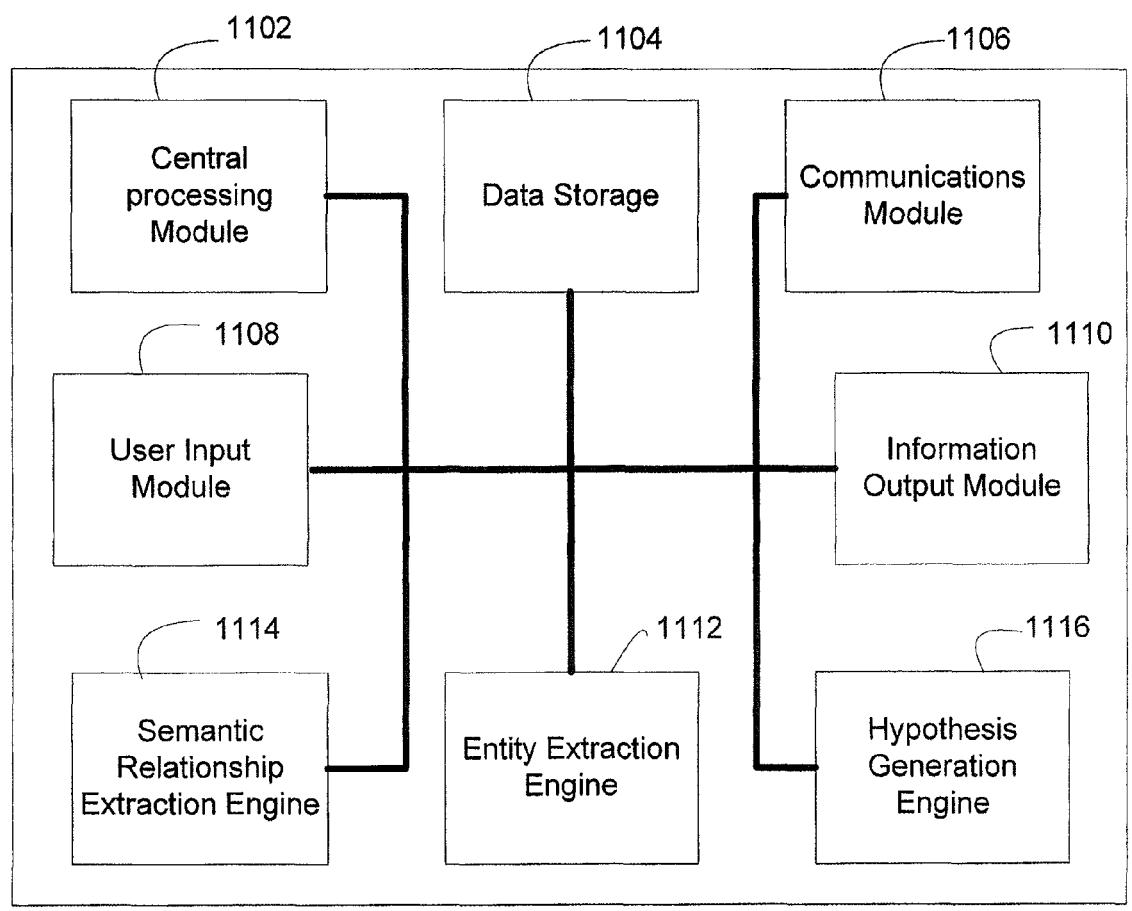

Having thus described the invention in general terms, reference will now be made to the accompanying drawings, which are not drawn to scale, and wherein:

FIG. 1 is a flow diagram that shows some embodiments of the present invention that generate hypotheses and facts by extracting semantic relationships from text data;

FIG. 2 is a flow diagram that shows some embodiments of the present invention that extract entities from a knowledge set;

FIG. 3 is a flow diagram that shows some embodiments of the present invention that extract semantic relationships of entities;

FIG. 4 is a flow diagram that shows some embodiments of the present invention that implements various hypothesis generation algorithms;

FIGS. 5A-8 are co-occurring concept relation diagrams that show various ways of associating different concepts;

FIGS. 9-11 are schematic diagrams of exemplary systems and apparatuses that can implement the methods of embodiments of the present invention.

DETAILED DESCRIPTION OF THE DRAWINGS

Text mining and information extraction tools are indispensable to overcoming the information overload discussed above. Information extraction tools are used to extract important facts from documents in response to a user query. If, for example, a researcher is interested in knowing all the protein interactions for a protein, information extraction tools can be configured to extract a list of protein interactions from all the relevant documents and thereby allow the researcher to avoid the need to read all these documents. Text mining is the science of discovering knowledge from a text corpus. Text mining (or data mining, when done electronically) computes associations between different facts that may be of interest to a user. For example, text mining can allow a computer to discover new, previously unknown information, by automatically extracting entities from information of different plain-language resources. Embodiments of the present invention also include the ability to link together entities extracted from various resources, and form new facts or new hypotheses, which can be explored further using various means of analysis.

More specifically, information extraction tools, such as ones provided by embodiments of the present invention, can extract knowledge from electronic versions of plain language text documents. These tools may be extremely valuable for researchers and society as a whole. For example, in the biomedical field alone, discovery of cures for diseases (such as AIDS and Cancer) could potentially be rapidly expedited by utilizing embodiments of the present invention, in particular by extracting semantic relationships and generating hypotheses of potential protein-protein interactions. The embodiments of the present invention overcome a number of complex technical problems that have inhibited information extraction from natural language text from being fully and reliably used by researchers (or anybody else).

The goal of information extraction is to generate previously unknown information and/or generate previously unknown associations (among pieces of known or unknown information), using known existing information from a large number of electronically-stored text documents. Some embodiments of the present invention comprise outputting (e.g., presenting on a display screen, saving to a local storage device, uploading to a remote database, etc.) the generated information and/or associations (the combination of which may be knowledge) to a user in the form of one or more hypotheses and/or facts. (As used herein, the difference between hypotheses and facts is the amount of further testing that would be required to confirm the validity of the outputs. Hypotheses would require additional experimentation to confirm their validity, whereas facts can be confirmed based on logic and the previously known information and/or associations.)

Many embodiments of the present invention also seek to reduce the relatively high percentage of irrelevant or false information and associations that plague previous information extraction systems and methods. Among other things, a highly accurate hypothesis generation system (such as those in accordance with embodiments of the present invention) can be used to integrate several technologies (or fields of study) when providing the context of the associated concepts that form the hypothesis.

Information extraction often involves breaking down the information (of sentence or paragraph) into its entities. The activity of extracting entities of interest (or potential interest) from a given piece of text is referred to herein as entity extraction. An example of a text is a news article, patent document, research paper, or other piece of written work. Examples of entities include names of people, companies, diseases, symptoms, proteins, chemicals, drugs, etc. Moreover, relationship types between entities can also be extracted from a piece of text, which is referred to herein as relationship extraction. As such, many of the embodiments of the present invention help eliminate various disadvantages of previous systems, including the previous systems' scalability limitations and inability to generate hypotheses beyond the initial concepts provided by the users, some of which are mentioned above.

Information extraction from natural language text involves systematically parsing through ("reading") and analyzing thousands upon thousands (if not millions) of electronic documents, in some instances on a sentence-by-sentence basis. One form of information extraction is a binary relationship extraction. For example, binary relationship extraction can be useful for developing less complicated facts. More specifically, a binary relationship extraction can be utilized if a user just wants to determine what individuals are publicly known as being part of an organization, or not part of organization.

However, despite the complexities inherent to all information extraction analyses, a binary relationship-type information extraction often disregards much pertinent information when applied to other fields of study, such as the biomedical field of study. An example of a binary relationship in the biomedical field is whether two proteins interact or not. This approach does not scale well when there can be, for example, multiple unknown types of interactions between various proteins.

Some embodiments of the present invention overcome these obstacles by implementing a multi-class relationship extraction protocol. Some of the multi-class relationship extraction protocols use subsequences of words as features for multi-class relationship extraction, and are discussed further below. Additionally, some of the protocols automatically extract subsequences composed of, for example, words, part of speech (POS) tags, and semantic types (categories).

Some embodiments of the present invention now will be described with reference to the accompanying drawings, in which some, but not all embodiments of the invention are shown. Indeed, the present invention may be embodied in many different forms and should not be construed as limited to the embodiments set forth herein; rather, these embodiments are provided so that this disclosure will satisfy applicable legal requirements. For example, with regards to the processes discussed herein, some of the steps can be omitted, rearranged, replicated, divided, repeated and/or replaced with other steps not explicitly discussed herein. In addition, like numbers refer to like elements or steps throughout.

FIG. 1 shows an exemplary method, process 100, that is consistent with at least some embodiments of the present invention for generating hypotheses (or facts) by first extracting semantic relationships from text data (i.e., data that is used to represent textual information). Although only exemplary, process 100, like the other processes and algorithms mentioned herein, is designed to be implemented by one or more systems or apparatuses, comprising various electrical components that are consistent with embodiments of the present invention. (Examples of such systems are discussed more herein, such as in connection with, e.g., FIGS. 9-11) Process 100 starts at step 102, and then proceeds to step 104.

At step 104, process 100 waits for an input representing a user's interaction with an input component. For example, process 100 can wait for the user to define at least one knowledge set (e.g., one or more databases of documents dedicated to a specific topic, such as those that are included in the Unified Medical Language System maintained by the United States federal government). The user can also enter, for example, instructions that command the system as to the particular type or types of processes the user would like the system to execute. As yet another example, the user can input general parameters that define the bounds and/or variables required by the subsequent steps of process 100.

Next is step 106, at which a determination is made as to whether or not the necessary user input has been received. If the necessary user input has not been received, a determination is made at step 108 as to whether or not the system has timed out. If the system has timed out, process 100 ends at step 110. If the system has not timed out, process 100 returns to step 104.

If, at step 106, a determination is made that all of the necessary user inputs have been received, process 100 advances to step 112. At step 112, the procedures for extracting the entities included in each sentence of the knowledge set are extracted. A number of methods can be used to extract an entity. FIG. 2 shows an exemplary embodiment of a method that can be used to extract the entities from a knowledge set. In particular, FIG. 2 shows the Dictionary Search method. Some embodiments of the invention could also be configured to utilize the ABNER process, which stands for "A Biology Named Entity Recognizer" and is a software tool designed for molecular biology text analysis, any other process, or combination thereof. (Although many examples used herein are focused on entities related to the biomedical field, one skilled in the art will appreciate that this approach, like any other approach or system discussed herein, can be applied to other types of entities.)

As used herein, an entity is a word or phrase (i.e., group of words) that the system determines to be (at least potentially) relevant to the knowledge set and/or a potential hypothesis. The following are a few examples of entities that a system may determine are related to each other and extract.

Example sentence one: "The effect of megestrol acetate on anorexia, weight loss and cachexia in cancer and AIDS patients (review)."

In example sentence one, when taken alone, the relationship between the italicized entities may be vague to the system. However, the systems and methods of embodiments of the present invention can leverage the entities of other sentences that are included in the knowledge set, to make a determination as to the relationship between entities. Accordingly, the methods and systems of embodiments of the invention allow for the monitoring and logging of each occurrence of the entities (after the entities are initially identified). The following sentence, for example, helps show what are "entities" based on how the entities might be related, which leads to the system being able to better "learn" and "understand" the knowledge set.

Example sentence two: "Megestrol acetate oral suspension is approved by the Food and Drug Administration for the treatment of anorexia, cachexia, or unexplained significant weight loss in patients with AIDS." In example sentence two, the relationship is considered to be treatment between the italicized drug and disease.

Next in process 100 is step 114, at which the system begins executing the procedure(s) for extracting semantic relationships from the data or knowledge sets; (One or more of the knowledge sets may have been identified by the user while waiting at step 104, preconfigured by the user previously, or automatically selected by the system implementing process 100.) One of the previously received inputs may have also defined the type of procedures to be used by the system to extract the semantic relationships from the knowledge set(s).

For example, there are at least two different methods of semantic relationship extraction that the system can utilize and/or that a user can instruct the system, or a component thereof (e.g., the system's extraction engine), to implement. The first exemplary method of extracting semantic relationships is referred to herein as the Discriminative Token Subsequences Classifier approach, which is discussed more in connection with, e.g., FIG. 3. A second exemplary method for extracting semantic relationships is referred to herein as the Token Subsequence Kernel approach, which is primarily employed during multi-class relationship extractions of text-based semantics and is discussed more below. Both of these exemplary methods use subsequences of tokens as features and support vector machines as the classifier. The semantic relationship extraction methods discussed below, can be used on at least two knowledge sets or data sets. As used herein, a data set is a broader category of electronic data as compared to, e.g., a knowledge set. A data set can include, for example, protein-protein interaction data from the BioText group of the University of California, Berkeley and/or drug-drug relationship data collected elsewhere and stored locally. Additional relationship extraction algorithms, which are not discussed in greater detail herein, can also be implemented at step 114. The additional relationship extraction algorithms include, for example, the Rule-based approach (which uses manually constructed language patterns to extract a particular type of interactions by comparing sentences to templates representing the patterns) and the Generative model approach (which use underlying graphical representations of probability distributions that have nodes representing random variables and arcs representing conditional independence assumptions).

At step 116, a determination is made as to whether the extraction of the semantic relationships and entities were successful. If the extractions were not successful (e.g., the system timed-out, an error was encountered, nothing was identified for extractions, etc.), process 100 proceeds to step 118, at which the user is notified that the extraction was unsuccessful, Step 118 may include utilizing a display component, speakers, other user interface module and/or communications module to send a failure notification of the unsuccessful extraction to the user. Process 100 then returns to step 104 and waits for another input representing a user's interaction with an input component.

However, after determining at step 116 that the extraction was successful, process 100 proceeds to step 120. At step 120, one or more hypotheses generation algorithms are executed based on the extracted semantic relationships and/or extracted entities. Various algorithms and combinations of algorithms can be used to generate hypothesis. One such algorithm, referred to as the discovery-driven hypotheses generation approach (which is discussed more below in connection with, e.g., FIG. 4). The discovery-driven approach can be used simultaneously with other hypotheses generation algorithms (such as those discussed in connection with, e.g., FIGS. 5-8). The discovery-driven hypotheses generation approach is a systematic evaluation methodology.

Next is step 122, at which a determination is made as to whether the hypotheses generation algorithm or algorithms were successful. If the hypotheses generation algorithms were not successful (e.g., the system timed-out, an error was encountered, no facts or hypotheses were generated, too many facts or hypotheses were generated, etc.), process 100 proceeds to step 124, at which the user is notified that the extraction was unsuccessful, Step 124 may include utilizing at least one display component, speaker, other user interface component and module, as well as a communications module and component to send a failure notification of the unsuccessful hypotheses generation to the user. Process 100 then returns to step 104 and waits for another input representing a user's interaction with an input component.

However, after determining at step 122 that the extraction was successful, process 100 proceeds to step 126, at which the results are presented to the user. Like the failure notification, the results can be presented using any type of component and/or module. For example, one or more hypotheses, facts or combination thereof can be presented as textual information in the language of the user's choosing. That language may be different than the language or languages used to create the hypotheses and facts that are produced by process 100 and outputted by the system implementing process 100. Process 100 then returns to step 104 and waits for another input representing a user's interaction with an input component of the system.

FIG. 2 shows an exemplary embodiment of a method that can be used to extract the entities from a knowledge set, and is sometimes referred to herein as the Dictionary Search method. Process 200 starts at step 202, and then proceeds to step 204.

At step 204, process 200 identifies a first sentence. Some embodiments of the invention accomplish this step through use of a punctuation mark conventionally used to signify the completion of the first sentence. For instance, step 204 may use a period punctuation to identify the end of the sentence.

At step 206, process 200 divides the first sentence into tokens. A token may refer to an element belonging to the union of a set of words, a set of part of speech tags, and/or a set of semantic types.

At step 208, process 200 tags each token based on its part of speech. For example, if the token is an adjective, it may receive the tag "JJ" while a token that is a noun may be tagged "NNS".

At step 210, process 200 chunks, or groups, the tokens into phrases. Some embodiments of the invention accomplish this step by determining the relationship between each token in the first sentence based on their respective tag.

One technique for implementing each of steps 206, 208, and 210 of process 200 may be to utilize a natural language processing tool. The natural language understanding system of such a tool allows the conversion of human language representations into representations that allow for easier manipulation by the system. Thus, the system can identify each token, identify and tag the part of speech of each token based on its relationship to the other tokens in the first sentence, and properly chunk the tokens into phrases.

At step 214, process 200 identifies the phrase or phrases as an entity or entities in the first sentence by searching for the phrase or phrases in a dictionary. Some embodiments of the invention perform this step by identifying the phrase's type. For example, a noun phrase that that is a sequence of adjectives followed by a noun form may be given the phrase type "Adjective-Noun Pattern". Alternatively, the phrase type may be classified by its tags (e.g. an "Adjective-Noun Pattern" may be given the phrase type "JJ JJ NNS").

When entities that conform to adjective-noun pattern are searched in the dictionary, it is possible that the phrase may not be identified as an entity if the dictionary contains only the noun. In order to handle such cases, the noun phrase may be verified for the adjective-noun pattern. If the phrase conforms to this pattern, then the last token (a noun) may be searched in the dictionaries. If the last token is found, then the noun phrase may be extracted as an entity. The type of the phrase is same as that of the last token.

If the noun phrase does not conform to this pattern, then substrings of the noun phrases may be generated to search in the dictionaries. The generation of substrings may be done in way to extract the longest possible entity within the noun phrase. For example, if "Chlamydia trachomatis infection" is the noun phrase which was not found in the dictionaries, the following substrings may be generated in the order to search in dictionaries: "Chlamydia trachomatis", "Chlamydia", "trachomatis infection", "trachomatis", and "infection".

At step 216, process 200 begins to filter out irrelevant entities based on their semantic types. For example, a dictionary may contain entities related to organizations, country names, and so forth. Such entities are not helpful for the relation extraction classification task. Hence, filtering the extracted entities from the intermediate results is an important task. The semantic types of the entities are used to filter out the irrelevant entities.

There can be numerous ways to determine the irrelevancy of a semantic type of an entity. In some embodiments of the invention, the irrelevancy of a semantic type may be determined by a predefined list of irrelevant semantic terms. These predefined terms may be generally set, or may be specifically mapped to the dictionary searched. For example, when the entities are searched for in the UMLS Metathesaurus, there are about 150 semantic types to which all the entities in the Metathesaurus are mapped. Conversely, a user may define a list of semantic types as relevant that may otherwise be determined irrelevant at step 216.

At step 218, process 200 extracts the unfiltered entities. Then, at step 220, process 200 determines if there is another sentence to be tokenized. If step 220 finds that there is another sentence to be tokenized, it repeats steps 204 to 220. If not, process 200 ends at step 224.

A first exemplary method (mentioned above in connection with, e.g., step 114 of FIG. 1) for extracting semantic relationships is referred to as the Discriminative Token Subsequences Classifier approach. Some embodiments of this invention may be used on training sentences from protein-protein interaction data. For example, the BioText group of the University of California at Berkeley maintains an HIV-1 human protein interactions database. The database includes information about a pair of proteins (PP), the interaction types between them and Pubmed identification numbers of the journal articles describing the interactions. A pair of proteins (PP) can have multiple interactions, but a PP can be assigned a single interaction in a journal article or sentence. The combination of protein1, protein2, and the pubmed identifier is sometimes referred to here as a triple. A triple has an interaction type assigned to it. All the sentences of a triple are assigned the same label. There can be a number of classes of interactions, such as the 10 shown in Chart 1 below. There may also be a number of sentences for each class of interaction, which is also shown in Chart 1 below.

CHART 1

| Interaction Type | Number of Sentences |
| --- | --- |
| Degrades | 123 |
| Synergizes with | 187 |
| Stimulates | 167 |
| Binds | 422 |
| Inactivates | 160 |
| Interacts with | 162 |
| Requires | 393 |
| Upregulates | 217 |
| Inhibits | 162 |
| Suppresses | 150 |

Here the goal is to assign a relationship to the triple. All the sentences are classified and assigned labels. A triple is assigned a label by choosing the most frequent class among the sentences of the triple. The data is divided into training and testing in such a way that all the sentences of a triple are used in either training or testing, that is triples used in training and testing can be different. For example, two thirds of the triples can be used for training and the remaining for the testing. One set of exemplary results for the following approaches are described as follows:

1. Discriminative common token subsequences method can be applied for sentence level training.
2. Discriminative common token subsequences method can be applied for triple level training.
3. Token subsequence kernel can be applied for sentence level training.
4. Token Subsequence kernel can be applied for triple level training.

FIG. 3 illustrates the Discriminative Token Subsequences Classifier approach, which is used to extract semantic relationships of entities. Process 300 starts at step 302 and proceeds to step 304. At step 304, process 300 receives a number of training sentences from the data set. For example, there may be n training sentences, $s_1, s_2, s_3 \ldots s_{n1}, \ldots s_{n2} \ldots s_{n3} \ldots s_n$.

At step 306, process 300 groups the training sentences into specified classes. Thus, for n training sentences, sentences from $s_1$ to $s_{n1}$ belong to class 1, sentences from $s_{n1+1}$ to $s_{n2}$ belong to class 2, and so on.

At step 308, process 300 selects a first class to be sequenced (e.g. class 1). At step 310, process 300 selects from this first class a first sentence to be sequenced (e.g. $s_1$).

At step 312, process 300 generates the subsequences for the selected sentence of the selected class, e.g., for sentence $s_1$, subsequences between $s_1$ and $s_2$, $s_1$ and $s_3$, $s_1$ and $s_4$, ..., $s_1$, and $s_{n1}$ are computed.

In some embodiments of the invention, the user may implement one or more rules to control the generation of these subsequences, e.g. specifying certain stop words, limiting the length of sequences, etc. Stop words are user-specified words that can be automatically removed from the sentences, e.g. prepositions such as "in", "or", "of", "after", etc. However, some of the words that a user may usually include in the stop words list can be removed if they are considered important keywords for the specific relation extraction task. For example, for the disease-treatment relation extraction task, patterns such as "Treatment for Disease" and "Disease after Treatment" may be observed. Hence the user may remove "for" and "after" from the stop words list.

The remaining non-stop words along with the corresponding part of speech (POS) tags may then be used to compute the subsequences. The user may also limit the length of sequences. The length of a subsequence between two sentences can vary from a single token to a sequence equivalent in length to one of the sentences (when a sentence contains another sentence). In such a case, the number of subsequences generated is exponential to the length of the sentences. Most of the relationships between the entities can be expressed in sequences of a maximum of four words. In many instances, a subsequence longer than five does not give any improvement in accuracy.

At step 316, a determination is made as to whether any other sentences within the class have yet to be subsequenced. If there remain any sentences to be subsequenced, process 300 returns to step 310 to select a next sentence from the class to generate subsequences.

If the generation of subsequences is complete, process 300 proceeds to step 318 to compute common subsequences of the selected class. In some embodiments of the invention, this step is performed in similar fashion to step 312 and may incorporate the same user implementations. For example, the user may indicate which stop words to use. The remaining, non-stop words along with their corresponding part of speech (POS) tags are used to compute the common token sparse subsequences.

A "token sparse subsequence" can be defined by the formula $$\Sigma_t = \Sigma_w \cup \Sigma_p \cup \Sigma_s$$

where $\Sigma$ is a finite alphabet and $S = S_1 S_2 \ldots S_{|s|}$ a sequence over $\Sigma$, and $$S_i \in \Sigma, 1 \leq i \leq |s|$$

where $i = [i_1, i_2, \ldots i_m]$, with $1 \leq i_1 < i_2 < \ldots < i_m \leq |s|$, is a subset of the indices in s and $s[i] = s_{i1} s_{i2} \ldots s_{im}$ is a subsequence of sequence s. Note that s[i] does not necessarily form a contiguous subsequence of s. These non-contiguous subsequences are called "sparse subsequences".

In the "token sparse subsequence" formula, $\Sigma_w$ are word sequences. For example, S=Knowledge is divine is a word sequence generated from $\Sigma_w = \{\text{"Knowledge," "is," "divine"}\}$. A sparse word subsequence of s given above is "Knowledge divine" and i=[1, 3].

The sequences defined over $\Sigma_p$ are called part of speech (POS) sequences. For example, the sentence "Knowledge is divine" becomes Knowledge/NN is/VBZ divine/JJ. The part of speech sequence for the sentence is p=NN VBZ JJ defined over $\Sigma_p = \{\text{NN, VBZ, JJ, DT, VBN, } \ldots\}$.

$\Sigma_s$ is a finite set of semantic types. The semantic types may be, for instance, the same as an onthology such as the Unified Medical Language System (UMLS) semantic types. The UMLS semantic types have a predefined set of categories for medical concepts. For example, $\Sigma_s = \{\text{"Disease or Syndrome," "Amino Acid, peptide or protein," "Neoplastic process," } \ldots\}$.

A common pattern found in the text to express a semantic relation between two entities contains a verb between the two entities. Protein-verb-protein is a frequent pattern in sentences where two proteins interact. When there are several example sentences expressing a type of relationship between two entities, the patterns which are made up of only words will not satisfy all the sentences. However if the patterns are built from not only words but also from part of speech tags, there is a good chance of generating frequent patterns. Since the part of speech tags are general categories, patterns containing both words and part of speech tags can be considered as a generalization of the patterns which contain only words. Specific patterns are more useful to classify multi-way relationship problems. The chart 2 below shows examples of patterns:

CHART 2

| Patterns | Generalized pattern |
| --- | --- |
| "Protein-A interacts with Protein-B" "Protein-A binds to Protein-B" "Protein-A inhibits Protein-B" | "Protein-A verb Protein-B" |

At step 320, process 300 stores the common subsequences of the selected class. Some embodiments of the invention store the generated common subsequences in a matrix. A particular example of such a matrix is a Pattern-Sentence Matrix.

In the pattern-sentence matrix, rows correspond to common subsequences, also sometimes referred to as patterns, columns correspond to sentences. A similar matrix, term-document matrix can be used in information retrieval. A term-document matrix is a matrix with rows corresponding to terms and columns corresponding to documents. The Pattern-Sentence matrix is updated once after computing the common patterns between two sentences belonging to the same class. An example pattern-sentence matrix with 3 classes and 2 sentences in each class is shown below. The cell values, w(i,j) represent the weight of a pattern (subsequence) in a sentence. An example pattern-sentence matrix is shown Chart 3 below:

CHART 3

|  | Class 1 | | Class 2 | | Class 3 | |
| --- | --- | --- | --- | --- | --- | --- |
| Pattern | s1 | s2 | s3 | s4 | s5 | s6 |
| 1. TREAT for DIS | w(1, 1) | w(1, 2) | w(1, 3) | w(1, 4) | w(1, 5) | w(1, 6) |
| 2. TREAT DIS | w(2, 1) | w(2, 2) | w(2, 3) | w(2, 4) | w(2, 5) | w(2, 6) |

CHART 3-continued

|  | Class 1 | | Class 2 | | Class 3 | |
| --- | --- | --- | --- | --- | --- | --- |
| Pattern | s1 | s2 | s3 | s4 | s5 | s6 |
| 3. DIS after TREAT | w(3, 1) | w(3 2) | w(3, 3) | w(3, 4) | w(3, 5) | w(3, 6) |
| 4. DIS TREAT | w(4, 1) | w(4, 2) | w(4, 3) | w(4, 4) | w(4, 5) | w(4, 6) |
| 5. TREAT prevent DIS | w(5, 1) | w(5, 2) | w(5, 3) | w(5, 4) | w(5, 5) | w(5, 6) |

The weight of a pattern within in a sentence, w(i,j), is computed based on two criteria used in String kernels: (1) the weight should decrease as the gaps increase within the pattern; and (2) the weight of a pattern is directly proportional to the frequency of a pattern. In other words, weight is inversely proportional to sparseness of a pattern.

The weighting formula is as follows: If p is a pattern and s is a sentence then w(p, s) is the weight of the pattern p in sentence s:

Let $i_k=[i_1, i_2, \ldots i_m]$ be one of the m index sequences of the pattern p in sentence s.

Let $l_p$ represent the length of the pattern.

$$w(p, s) = \sum_{k=1}^{n} \lambda^{l(ik)/lp} \text{ where } 0 \le \lambda \le 1$$

$l(i_k)$ represents the length of the index sequence $i_k$.

For example, p="TREAT for DIS" is a pattern (subsequence) of semantic types, $l_p=3$, s=<TREAT> gemcitabine and carboplatin </TREAT> for patients with <DIS> advanced non-small cell lung cancer </DIS>, $i_k=[0, 1, 4]$, and $l(i_k)=5$.

For $\lambda=0.5$, $w(p,s)=0.5^{5/3}=0.314$.

At step 322, process 300 determines if there are any other classes that have yet to be subsequenced. If no, process 300 ends at step 330. If yes, step 324 determines if there are a sufficient number of sentences that have been subsequenced to complete the training phrase, which can be, for example, two thirds of the total number of sentences in the class.

If at step 324, there are a sufficient number of sentences subsequenced to complete the training phrase, process 300 proceeds to step 326 to determine if a feature selection algorithm has been executed.

One of the goals of feature selection is to remove irrelevant or inappropriate attributes from the representation. Feature selection improves computational efficiency of the system. As the number of features increase, the training time and also the testing times increase. Since the training is done only once, training time is not as important of a factor in favor of feature selection. However, the classification time (testing time) is an important factor when implementing some embodiments of the hypothesis generation algorithms of the present invention, because this is the time incurred by the system when used for the classification in real time.

If at step 326, process 300 determines that a feature selection algorithm has been executed, it returns to step 308 to select a class that has yet to be subsequenced. If at step 326, process 300 determines that a feature selection algorithm has not been executed, it proceeds to step 328 and executes one or more feature selection algorithms.

Some embodiments of the invention can utilize the Chi-Square test as a feature selection algorithm. A Chi-Square test is used to compute a score for a pattern (subsequence) for each of the classes. The score reflects the dependence between a pattern and a class.

$$X^2(t,c)=N \times (AD-CB)^2/(A+C) \times (B+D) \times (A+B) \times (C+D)$$

A=Number of instances in which both the class and the feature occur.

B=Number of instances in which the class occurs with out the feature.

C=Number of instances in which the feature occurs with out the class.

D=Number of instances in which both feature and class do not occur.

N=Total number of instances.

Pattern-Sentence matrix has the patterns (features) and their weights for all the sentences. Chi-Square scores are computed for all the patterns in the Pattern-Sentence matrix. A high value of Chi-Square for a pattern "t" and class "c" means the pattern "t" is a discriminatory pattern that can help in distinguishing a sentence belonging to class "c". All the patterns are ordered for each class according to their Chi-Square values. Here, feature selection is done by choosing only the top "k" patterns from the ordered list of patterns for every class. The Chi-Square measure is used to select the most distinguishing patterns for each class. The union of distinguishing patterns of all classes forms the feature set for both training and testing sentences.

If at step 322, process 300 determines that there are no other classes to be sequenced, the process ends.

A second exemplary method (mentioned above in connection with, e.g., step 114 of FIG. 1) for extracting semantic relationships is the Token Subsequence Kernel approach, which is primarily employed during multi-class relationship extractions of text-based concepts (entities). The dynamic programming formulation of the token sequence kernels is based on the following equations.

$$K'_0(s, t) = 1, \text{ for all } s, t$$

$$K'_i(s, t) = 0, \text{ if } \min(|s|, |t|) < i, (i = 1, \ldots n-1)$$

$$K_n(s, t) = 0, \text{ if } \min(|s|, |t|) < n,$$

$$K'_i(sx, t) = \lambda K'_i(s, t) + \sum_{j:t_j=x} K'_{n-1}(s, t[1:j-1]) \lambda^{|t|-j+2} (i = 1, \ldots n-1)$$

$$K_n(sx, t) = K_n(s, t) + \sum_{j:t_j=x} \lambda^2 K'_{n-1}(s, t[1:j-1])$$

The token sequence kernels compute the similarity between the two sequences using all the common subsequences of length "k". The kernel is defined as a linear weighted combination of subsequence kernels of length up to n as follows.

$$\overline{K}_n(s, t) = \sum_{i=1}^{n} \mu^{1-i} K_i(s, t)$$

Exemplary results of the Discriminative Token Subsequences method are shown in U.S. Provisional Application No. 61/024,099 that is incorporated by reference in its entirety above, including the exemplary results of the Distributive Token Subsequences method, along with the other test results included in U.S. Provisional Application No. 61/024,099.

A token subsequence kernel uses semantic types to represent the entities from the text. Thus a sentence or a document becomes a sequence of words and semantic types when implementing the Token Subsequence Kernel approach. In the recursive dynamic programming formulation described above, when a word of sequence s is not equal to a word of sequence t, their corresponding part of speech tags are compared. Although different matching weights for different words can be incorporated into the kernel, embodiments of the present invention all the same formulation to be used to give different weights to words, semantic types and part of speech tags. In addition, in some embodiments of the invention, the same weights are used for all of them. One skilled in the art would appreciate that other approaches can be used to extract semantic relationships.

FIG. 4 elaborates on step 120 of FIG. 1. More specifically, FIG. 4 shows a first exemplary method, process 400, sometimes referred to as the Discover-driven approach, which is used to implement various hypothesis generation algorithms (such as those discussed below) based on previously extracted semantic relationships. Process 400 can be used in conjunction with, for example, the pairwise algorithm described in PCT/US07/063983, which this claims priority to and is incorporated by reference above. Even when used with the pairwise algorithm, process 400 emphasizes evaluation measures and therefore helps provide objective measures to evaluate the generated hypotheses, instead of just providing a list of the interesting hypotheses generated. Process 400 helps avoid the generation of a large number of spurious hypotheses, while providing results that have enough details to enable the user to understand and validate each hypothesis. Although search engines and inference engines can be used in conjunction with the results produced by process 400, process 400 seeks to reduce the frequency that a user will seek to use search engines and/or inference engines on the results.

Process 400 is a discovery-driven approach that starts at step 402. Next is step 404, at which co-occurring concepts (or related entities, tokens) and association rules are computed using, e.g., the methods discussed in connection with, e.g., FIGS. 2-3. The co-occurring concepts and/or association rules can be located at one or more different databases, such as those that maintain the MEDLINE documents. (The MEDLINE documents include more than 12 million documents, but the recent documents of the last few years are not included yet). By pre-computing all the concept associations from MEDLINE, the need to query and retrieve the documents from, for example, a Pubmed based on a user query is eliminated. The co-occurring concepts can be computed (or collected), for example, as documents are added to the various databases, periodically (e.g., once a week, once a year, etc.), or upon a user command to do so.

Subsequent to computing the co-occurring concepts and/or rules for the data included in the databases, at step 406, a user can interact with the system and cause the system to issue a hypothesis generation request command. The command can include one or more target databases, parameters, specific concepts (e.g., drug, disease, particular chemicals, etc.), among other things.

Next is step 408, at which hypotheses and facts are generated in response to the command issued at step 406. The hypotheses and facts are associated with the entities and semantic relationships previously extracted. The pairwise algorithm, for example, can still be used at step 406. But, because of step 404, instead of generating one or several hypotheses at one time based on the user's query, the hypotheses and facts come from the data embedded in the underlying literature database. Another advantage of using batch (or mining) mode is that this mode may generate hypotheses that are novel and cross fields of study, rather than being bounded by the user's initial hunch (as was the case in legacy systems and methods).

The representative code below describes the steps involved in computing the co-occurrence matrix L and binary association matrix M. L stores co-occurring document frequencies for all the concept pairs and M stores value one if an association satisfies both minimum support and minimum confidence threshold values.

Procedure-association: Creating concept co-occurrence matrix and binary association matrix.

1: Create a symmetric matrix L such that $l_{CC}$, represents the co-occurrence frequency of the concept C, represented by the ith row of L and the concept Cj represented by the jth column of L. for any matrix P, rowSizeP and colSizeP represent the number of rows and the number of columns in the matrix P respectively.
2: Create a matrix M with size rowSizeL × colSizeL.
3: for (i = 0; i < rowSizeL; i++) do
4:    for (j = 0; j < colSizeL; j++) do
5:       if $l_{CCj}$ < minSupport or $$\left( l_{CCj} \bigg/ \sum_j l_{CCj} \right) < \text{minConfidence then}$$

Figure 5A:
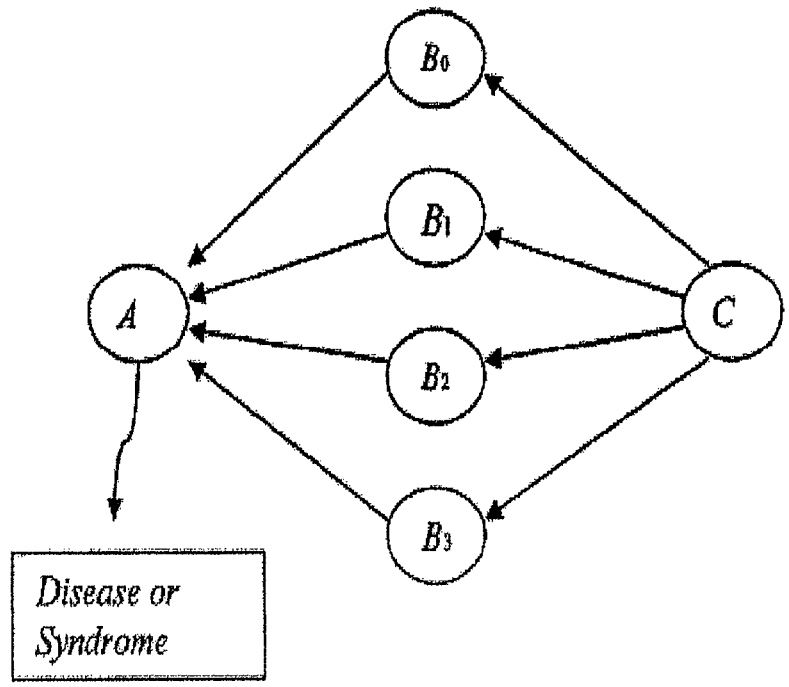
Figure 5B:
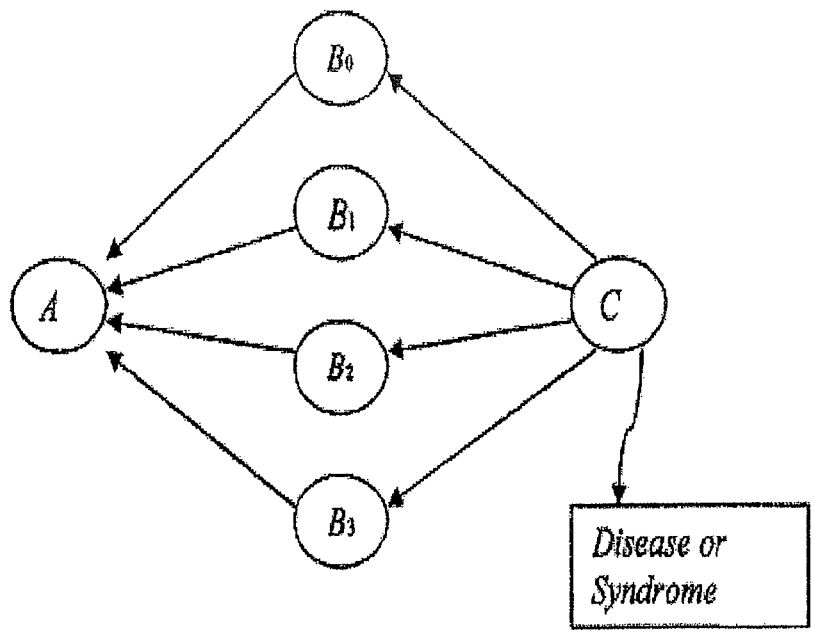

6:          $M_{CCj} = 0$
7:       else
8:          $M_{CCj} = 1$
9:       end if
10:    end for
11: end for Below is the representative code for the Pairwise hypothesis algorithm, which is based on the ABC model that is shown in FIGS. 5A and 5B. In this model, novel connections between two concepts A and C are attempted to be found, despite not co-occurring together, by using a common intermediate concept B. The inference rule used in this model is: If A→B and B→C, then A→C is a hidden connection. The pairwise algorithm, described below and incorporated by reference above, uses the same inference mechanism. In order to filter spurious and biologically irrelevant hypotheses, several constraints are introduced into the algorithm. The semantic types of the concepts should belong to one of the desired semantic types and the concepts should be leaf level concepts in the MeSH vocabulary. Algorithm-pairwise describes the steps involved in pairwise hypothesis generation. The matrix L is a concept co-occurrence matrix, with document frequency as the co-occurring count for concept pairs. M is a binary association matrix, in which a non-zero value of the cell $M_{CCj}$ represents an association rule $C_i \rightarrow C_j$ whose support is greater than or equal to minSupport and confidence is greater than or equal to minConfidence. The matrix N is the second order association matrix. The pairwise hypothesis generation algorithm is described below.

| Pairwise Hypothesis Generation Algorithm |
| --- |
| Input: the concept co-occurrence matrix L and the binary association matrix M generated in Procedure-association.<br>Output: the set of candidate pairwise hypotheses.<br>1: Create a matrix N such that $N = M^T M$<br>2: for (i = 0; i < rowSizeN; i++) do<br>3:    for (j = 0; j < colSizeN; j++) do<br>4:        if $n_{C_iC_j} >$ minSupport2rd and $l_{CC_j} <$ minSupport then<br>5:            Output $C_i \rightarrow C_j$ as a candidate pairwise hypothesis.<br>6:        end if<br>7:    end for<br>8: end for |

If A's semantic type is "Disease or Syndrome" (as shown in FIG. 5A) and the semantic type of C is not "Disease or Syndrome" but one of the other desired semantic types, then the pairwise hypothesis is considered to belong to Case A.

Where as if C's semantic type is "Disease or Syndrome" (as shown in FIG. 5B) and semantic type of A is not "Disease or Syndrome" but one of the other desired semantic types, then the pairwise hypothesis is considered to belong to Case C.

Figure 6:
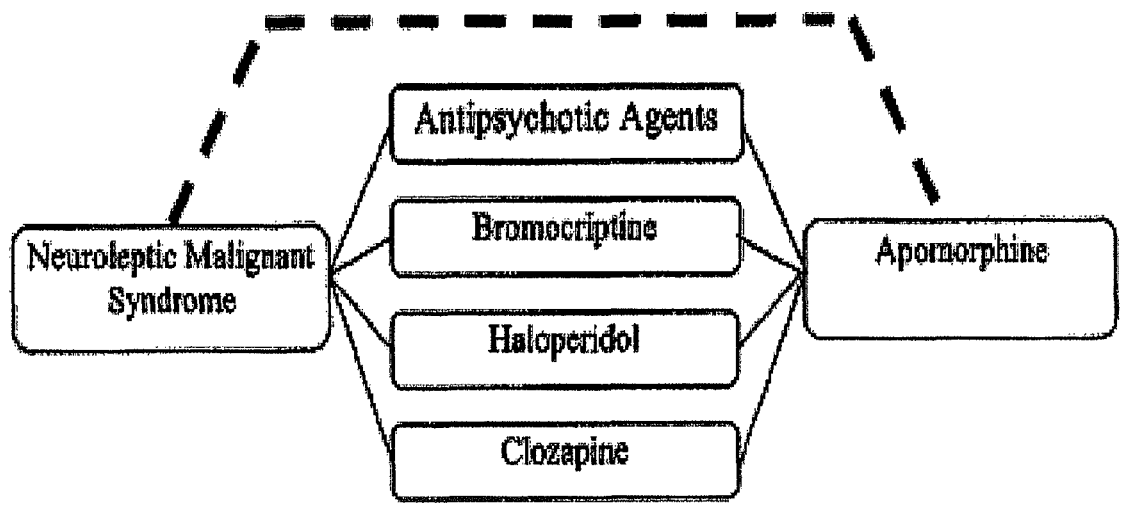

An example hypothesis generated from the pairwise hypothesis is shown in FIG. 6. In this example, the concept pair "Apomorphine" and "Neuroleptic Malignant Syndrome" has a strong relationship in the second order association matrix N, while it has a weak relationship in the co-occurrence matrix L. The associations "Apomorphine→Antipsychotic Agents," "Antipsychotic Agents→Neuroleptic Malignant Syndrome," "Apomorphine→Bromocriptine," "Bromocriptine→Neuroleptic Malignant Syndrome" have a non-zero value in the first order association matrix M.

Figure 7:
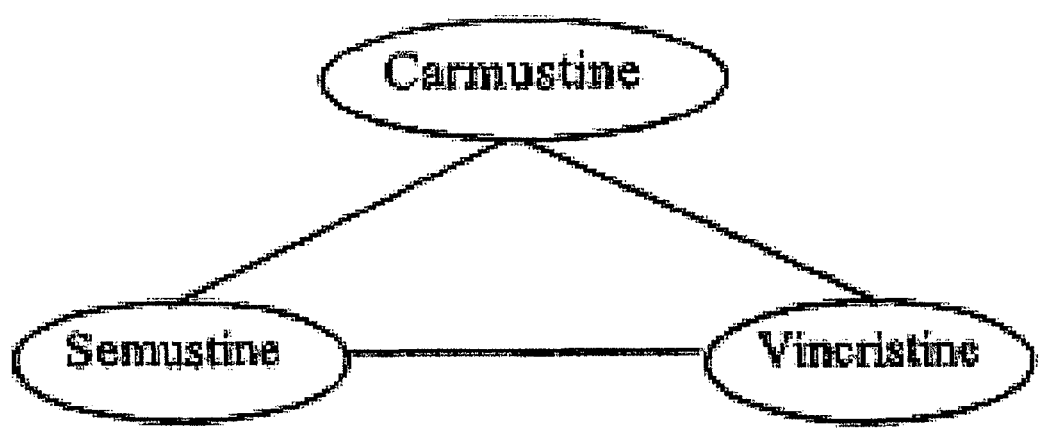
Figure 8:
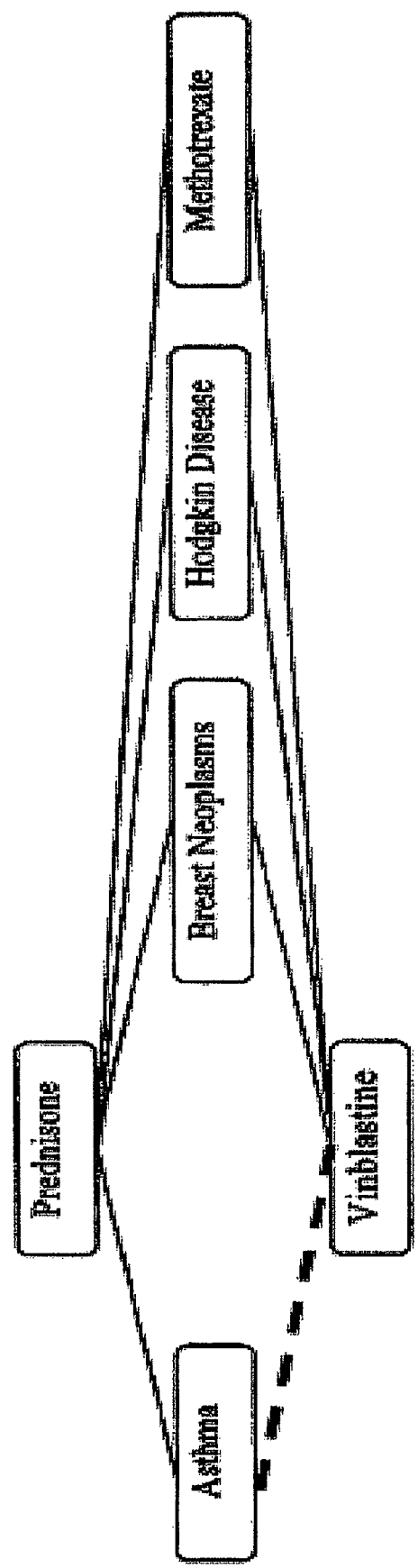

Another example of a hypothesis generation algorithm that could be implemented in conjunction with process 400 is the Chain Hypothesis Algorithm. The basic inference rule for chaining is that, "if concept A relates to B, B relates to C, and A relates to C, then A, B, and C may be related altogether," an example of which is shown in FIG. 7. This type of hypothesis may help identify chaining relationships among chemical compounds, predict biological pathways, and analyze combinational effects of drugs. If concepts A and B are strongly associated, concepts B and C are strongly associated, concepts A and C are also strongly associated and the concepts A, B and C together appeared in very few documents, the algorithm proposes the triple A-B-C as a chain hypothesis. The concepts should also belong to certain semantic categories. Exemplary code for the chain hypothesis generation algorithm is below.

| Chaining Hypothesis Generation Algorithm |
| --- |
| Input: the binary association matrix M generated in Procedure-association.<br>Output: the set of candidate chaining hypotheses.<br>1: for (i = 0; i < rowSizeM; i++) do<br>2:    for(j = 0; j < colSizeM; j ++) do<br>3:        if $M_{CC_j} = 1$ and $C_i, C_j$ belong to the same desired semantic type then<br>4:           for (k = 0; k < colSizeM; k++) do<br>5:               if $M_{C_jC_k} = 1$ and $C_j, C_k$ belong to the same desired semantic type then |

| Chaining Hypothesis Generation Algorithm (continued) |
| --- |
| 6:                if $M_{C_jC_k} > 0$ then<br>7:                   Calculate the co-occurrence frequency for triple $C_i$, $C_j$, and $C_k$ altogether and denote it as $freq_{C_iC_jC_k}$.<br>8:                if $freq_{C_iC_jC_k} <$ maxSupport3 then<br>9:                   Output Ci, Cj, Ck as a candidate chaining hypothesis.<br>10:               end if<br>11:              end if<br>12:           end if<br>13:          end for<br>14:        end if<br>15:    end for<br>16: end for |

In the above code and the example of FIG. 7, Vincristine and Carmustine are chemotherapy drugs given as a treatment for some types of cancer. Articles also show that Carmustine and Vincristine are used in combination chemotherapy. Semustine is an investigational chemotherapy drug and articles show its use in combination with Vincristine. However, there has not been any evidence of all three drugs being used in combination and thus the output of the algorithm suggests this as a hypothesis.

A third example of an algorithm that can be used in connection with process 400 is the substitution hypothesis generation algorithm, which looks for pairs of concepts such that concepts in a pair are similar to each other. Two concepts A and C are considered to be similar if a number of conditions are satisfied, such as, for example: (1) the semantic types of the two concepts are the same or very similar; (2) the two concepts are frequently co-occurring; and/or (3) the two concepts should have a sufficient number of commonly associated concepts. From this information, a context similarity score can be computed using their associated list of concepts. If a concept B is associated with only A, but not associated with concept C and the semantic type of concept B is one of the desired semantic types, then the system will hypothesize that concept C may be used as a substitute for concept A with respect to concept B. In some embodiments of the invention, A and C are required to be of the semantic type (e.g., drugs) and B of a different semantic type (e.g., disease). The intuition behind this algorithm is to mine those drug concepts that are closely related to already known drugs for a disease, but not yet reported in the literature of that disease.

An example of code representing the substitution hypothesis generation algorithm is described below.

| Substitution Hypothesis Generation Algorithm |
| --- |
| Input: the concept co-occurrence matrix L and the binary association matrix M generated in Procedure-association.<br>Output: the set of candidate substitution hypotheses.<br>1: for (i = 0; i < rowSizeM; i++) do<br>2:    for (j = 0; j < colSizeM; j++) do<br>3:        if $M_{C_iC_j} =$ l and a, a belong to the same desired semantic type such as drugs then<br>4:           Call procedure-similarity to calculate the similarity between concept $C_i$ and $C_j$ that is denoted as $sim(C_i, C_j)$.<br>5:           if $sim(C_i, C_j) >$ minSim then<br>6:               Create a set of concepts called CiAssoc, such that for the kth concept in $C_i$Assoc, denoted as $C_k$, we have $MC_iC_k = 1$.<br>7:               Create a set of concepts called $C_j$Assoc, such that for the kth concept in $C_j$Assoc, denoted as $C_k$, we have $M_{C_jC_k} = 1$. |

-continued

| Substitution Hypothesis Generation Algorithm | |
|---|---|
| 8: | let a set of concepts $C_i$Assoc_minus_$C_j$Assoc = $C_i$Assoc − $C_j$Assoc |
| 9: | for each concept $C_k$ in $C_i$Assoc_minus_$C_j$Assoc do |
| 10: | if $C_k$ belongs to a desired semantic type and $l_{C_jC_k}$ < minSupport then |
| 11: | Output concept $C_j$ as a candidate substitution of concept $C_i$ on concept $C_k$. |
| 12: | end if |
| 13: | end for |
| 14: | end if |
| 15: | end if |
| 16: | end for |
| 17: end for | |
| Procedure-similarity: calculate the similarity between two concepts A and B | |
| Input: the concept co-occurrence matrix L and the binary association matrix M generated in Procedure-association; concepts A and B | |
| Output: sim(A, B) | |
| 1: Create a set of concepts called AAssoc, such that for the ith concept in AAssoc, denoted as $C_i$, we have $M_{AC_i}$ = 1. | |
| 2: Create a set of concepts called BAssoc, such that for the ith concept in BAssoc, denoted as $C_i$, we have $M_{BC_i}$ = 1. | |
| 3: ABAssoc = AAssoc ∩ BAssoc | |
| 4: Create a vector called AContext, such that the ith number in AContext equals to | |
| $l_{AC_i} / \sum_j l_{C_iC_j}$, where $C_i$ is the ith concept in ABAssoc. | |
| 5: Create a vector called BContext, such that the ith number in BContext equals to | |
| $l_{BC_i} / \sum_j l_{C_iC_j}$ where $C_i$ is the ith concept in ABAssoc. | |
| 6: Output sim(A, B) = (AContext, BContext). | |

Another example of an algorithm that can be used in conduction with process 400 consistent with embodiments of the present invention is the substitution hypothesis generation algorithm. Like shown in the example of FIG. 8, both concepts "Vinblastine" and "Prednisone" have strong relations with quite a few common concepts including "Methotrexate," "Breast Neoplasms," "Hodgkin Disease," "Cancer Staging," "Cyclophosphamide," and many others. In addition, both these two concepts belong to the category "Drugs." "Asthma" is one of the concepts that is only associated with "Prednisone" but not with "Vinblastine". Furthermore, "Asthma" belongs to one of the desired semantic types, which is "Disease." The hypothesis is that "Vinblastine" may be a substitution for "Prednisone" on "Asthma." This hypothesis is visualized in FIG. 8. On the right side of the middle column, it shows those concepts that both "Prednisone" and "Vinblastine" have strong relations with; while on the left side, it shows concepts that have strong relation only with "Prednisone" but not "Vinblastine." The dashed line represents the potential relationship of the two concepts.

One of the major problems faced by literature based hypotheses generation systems is the difficulty in evaluation. There is no formal definition of usefulness or accuracy of these systems. Most of the research work done in the field tries to validate the hypotheses by a domain expert and publish correct and interesting hypotheses among the generated hypotheses. For example, prior to the present invention, it was common to manually review the literature supporting the extracted hypothesis for scientific plausibility and relevance. But such an approach is only useful to demonstrate the potential of the literature based discovery. Embodiments of the present invention provide a more systematic and automatic approach to evaluate the generated hypotheses.

Somewhat interestingly, there has been little work actually committed to solving the idea of mining hypotheses from a document collection up to a cutoff date, and then subsequently verifying the hypotheses using a later document collection as a way of evaluation. Embodiments of the present invention include evaluation measures focused on this type of methodology. For example, in the information retrieval field, precision and the recalling of documents are used as the evaluation measures. Precision indicates how many documents among all the retrieved are relevant to the user query, and recall indicates how many relevant documents among all the relevant documents are retrieved. An objective measure of comparing information retrieval models is to compare their precision and recall values. In order to devise such measures of evaluation for hypotheses set, it is important to understand the desired properties of a hypothesis. Two of the most sought for properties are novelty and biological relevance. Both the properties are subjective, and finding an automatic way of measuring them is a difficult task, But, when hypotheses are generated retrospectively, that is using a subset of the document collection for generation and another subset of the document collection of later years for validation, it is possible to define concrete evaluation measures.

For example, a document collection can range from start_year to end_year. For a starting concept d, the set of strongly associated concepts can be extracted at any given year in the duration start_year_to_end_year. If the starting concept d is a disease, the set of associated drugs at any given time (T) can be extracted using the document collection from start_year to T. Let Assoc_Set(d, T) represent this set of existing connections for a given concept d at a time T.

New=Assoc_Set (d, T2)−Assoc_Set (d, T1) represents the set of all new connections established between the time period T2 and T1 for concept d. Precision and recall for a hypotheses generation algorithm can be as follows:

Recall(d, start_year, T1, T2)=Total Number of correct Hypotheses/|New|

Precision (d, start_year, T1, T2)=Total Number of correct Hypotheses/|H|

"H" is the set of hypotheses generated. A hypothesis is considered correct if the inference is found to be true in the document collections of later years. By defining these measures, it is possible to compare different hypotheses generation algorithms. It is also possible to fine tune the parameters used in a hypotheses generation algorithm. Exemplary test results are also included in Provisional Application No. 61/024,099, all of which are incorporated by reference.

FIG. 9 shows a block diagram of exemplary system 900 that can provide means for implementing the methods, procedures and code discussed herein. At the center of the system is a computing system 902, which can function as, among other things, a personal computer and/or server. Shown connected to the computing system 902 are several additional elements that may be separately connected to the computing system 902, interconnected by communications with the central computing system 902, or part of the computing system 902. One or more known reference sets 904 are available to the computing system 902. Data and/or information 906 representing existing content may be available to the computing system 902. A profile database 908 for storing associative relevancy knowledge profiles, such as those discussed in commonly-assigned PCT/US08/60984 (incorporated by reference above) and referred to herein as a knowledge repository may be available to the computing system 902. A user interface 910, such as a web-based ASP interface or standalone application, may be available to the computing system 902. The particular arrangements, connections, and physical localities of all of these systems and modules are not specific to the present invention, but simply that they can be used by some embodiments of the computing system.

Search engine 912 (or inference engine, or the like) may also be available to the computing system 902. Search engine 912 may be used for performing a discovery process operation upon one or more data and information sources, such as those discussed above. For example, a search engine may be used to search a data source using search terms and operators such as for a Boolean search. Similarly, an inference engine may be used to perform inference algorithms according to user entered criteria.

For example, FIG. 10 is a block diagram of a network framework 1000 that would benefit from embodiments of the present invention. Unlike the diagram of FIG. 9, which is representative of a more local or direct configuration, the diagram of FIG. 10 is representative of embodiments of the present invention which rely upon a network connection such as the Internet for availability and communication between elements of the system. For example, as shown in FIG. 10, each of the elements of the system may be separately located in interconnected through the Internet 1002 for substantiating an embodiment of the present invention.

Systems, methods, and computer program products of embodiments of the present invention can be implemented as local or direct configuration applications, such as generally represented by FIG. 9, as well as some networked configuration applications, such as represented in FIG. 10. It should be understood, however, that systems, methods, and computer program products of embodiments of the present invention can be utilized in conjunction with a variety of other configurations with various means of communication and connection. For example, systems, methods, and computer program products of embodiments of the present invention can be utilized in conjunction with wired and/or wireless connections and in local/direct and networked applications. For example, wired connections may include any one or more of an Ethernet connection, a serial (RS-232) connection, a parallel (IEEE 1284) connection, a USB connection, a SCSI connection, and other means of achieving a wired or contact electronic connection capable of providing communications between two computing devices. Wireless connections may include any one or more of radio frequency (RF), Bluetooth (BT), infrared (IR, IrDA), wireless LAN (WLAN, IEEE 802.11), WiMAX (IEEE 802.16), ultra wideband (UWB, IEEE 802.15), microwave ($\mu$), ultraviolet (UV), and other means of achieving a wireless, non-contact electronic connection capable of providing communications between two computing devices. Further, network applications can be of any variety, including without limitation a Local Area Network (LAN), a Campus Area Network (CAN), a Metropolitan Area Network (MAN): a Wide Area Networks (WAN), an intranet, and an extranet.

FIG. 11 is an exemplary block diagram of the functional schematics of computing system 902 shown in detail. Embodiments of the present invention provide modules, circuitry and other tools that allow a user (domain expert) to extract entities, extract semantics of the entities and generate hypotheses using a discovery-based algorithm. A selection of eight modules, which may include circuitry and/or software configured to implement the methods (or portions thereof) of the present invention are shown as being included in the computing system: central processing module 1102, data storage module 1104, communications module 1106, user input module 1108, information output module 1110, entity extraction engine 1112, semantic relationship extraction engine 1114, and hypothesis generation engine 1116.

Central processing module 1102 can include the hardware, circuitry, firmware and/or software that may be necessary to control each of the other components of computer system 902. For example, central processing module 1102 can include, for example, a central processing unit, firmware, a dedicated storage component, etc.

Data storage component 1104 is can include one or more storage devices and the circuitry, other hardware, software and/or firmware to facilitate the storing of electronic data (such as, e.g., flash memory, magnetic disk(s), and/or any other types of ROM/RAM). Data storage component 1104 can store, for example, search results, user entered parameters and information, data downloaded from a remote source (such as those discussed in connection with FIG. 10), commands, etc.

Communications module 1106 allows computing system 902 to communicate with remote devices, such as other computing systems, remote databases and servers. Communications module 1106 can include the circuitry, hardware, software and/or firmware required for one or more types of communication protocols (including, for example, Blue-Tooth, http, 802.11, etc.).

User input module 1108 can be used to enable physical signals generated by a user to be converted into electrical signals. For example, user input module 1108 can include the circuitry, hardware, software and/or firmware necessary to allow a user to use a computer mouse, keyboard, touchscreen display, and/or microphone. The user input module can facilitate the conversation of a physical input signal, which represents a user-entered command, into an electrical user input signal.

Information output module 1110 can be used to present information to a user, including the results of the hypothesis generation algorithms discussed above, or failure messages also discussed above. Information output module 1110 can include the circuitry, hardware, software and/or firmware necessary to display information (e.g., textual, graphical, or any other type of visual information), emit audio signals, and/or provide tactile feedback (such as vibrations).

Entity extraction engine 1112 can include the circuitry, hardware, software and/or firmware necessary to facilitate the extraction of entities from text data and implement the corresponding procedures (discussed above). In some embodiments, entity extraction engine 1112 functions as another module of computing system 902. In other embodiments, entity extraction engine 1112 is implemented in a device that is remote from computing system 902. In yet other embodiments, the functionality provided by entity extraction engine 1112 is distributed among both computing system 902 and remote devices.

Semantic relationship extraction engine 1114 can include the circuitry, hardware, software and/or firmware necessary to facilitate the extraction of semantics from the entities extracted by entity extraction engine 1114. Semantic relationship extraction engine 1114 can facilitate the implementation of the corresponding semantic relationship extraction procedures discussed above. In some embodiments, semantic relationship extracting engine 1114 functions as another module of computing system 902. In other embodiments, semantic relationship extracting engine 1114 is implemented in a device that is remote from computing system 902. In yet other embodiments, the functionality provided by semantic relationship extracting engine 1114 is distributed among both computing system 902 and remote devices.

Hypothesis generation engine 1116 can include the circuitry, hardware, software and/or firmware necessary to facilitate the generation of hypotheses and/or facts based on the various semantics extracted by semantic relationship extraction engine 1114 and the data supplied from data storage 1104 (and/or communications module 1106). Hypothesis generation engine 1116 can facilitate the implementation of the various hypothesis generation procedures discussed above. In some embodiments, hypothesis generation engine 1116 functions as another module of computing system 902. In other embodiments, hypothesis generation engine 1116 is implemented in a device that is remote from computing system 902. In yet other embodiments, the functionality provided by hypothesis generation engine 1116 is distributed among both computing system 902 and remote devices.

Many modifications and other embodiments of the invention set forth herein will come to mind to one skilled in the art to which these invention pertain having the benefit of the teachings presented in the foregoing descriptions and the associated drawings. Therefore, it is to be understood that the invention are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A hypothesis generation system, comprising:
   a communications module configured to communicate with a remote database, wherein the communications module facilitates the downloading of data from the remote database;
   a hypothesis generation module that is configured to:
      pre-compute co-occurring concepts included in the data prior to receiving a command to generate a hypothesis;
      generate a hypothesis based on the co-occurring concepts in response to receiving a hypothesis generation command; and
      transform the hypothesis into user-comprehendible results;
   a storage module configured to store the co-occurring concepts while awaiting the hypothesis generation command;
   a user input module configured to receive a user input and generate the hypothesis generation command; and
   a user interface module configured to present the user-comprehendible results on a display screen.

2. A method of generating hypotheses, comprising:
   communicating with a remote database;
   downloading data from the remote database;
   pre-computing co-occurring concepts that are included in the data, wherein the pre-computing occurs prior to receiving a user input that is associated with a command to generate one or more hypotheses;
   receiving the user input that is associated with the command to generate the one or more hypotheses;
   in response to a hypothesis generation engine receiving the command, generating at least one hypothesis based on the co-occurring concepts;
   transforming the at least one hypothesis into user-comprehendible results; and
   presenting the user-comprehendible results on a display screen.

3. A computer program product comprising a computer-readable storage medium having computer-readable program code portions stored therein and providing for hypothesis generation, the computer program product comprising:
   a first program code portion configured for communicating with a remote database;
   a second program code portion configured for downloading data from the remote database;
   a third program code portion configured for pre-computing co-occurring concepts that are included in the data, wherein the pre-computing occurs prior to receiving a user input that is associated with a command to generate one or more hypotheses;
   a fourth program code portion configured for receiving the user input that is associated with the command to generate the one or more hypotheses;
   a fifth program code portion configured for, in response to a hypothesis generation engine receiving the command, generating at least one hypothesis based on the co-occurring concepts;
   a sixth program code portion configured for transforming the at least one hypothesis into user-comprehendible results; and
   a seventh program code portion configured for presenting the user-comprehendible results on a display screen.

4. A method of generating a hypothesis comprising:
   extracting concept A, concept B, and concept C from a data set, wherein the extracting is performed by an entity extraction module specifically programmed to extract concepts from the data set;
   receiving the concept A, the concept B, and the concept C as inputs to a hypothesis generation module, wherein the hypothesis generation module is specifically programmed to generate a hypothesis;
   receiving as an input, at the hypothesis generation module, a semantic category associated with each of the concept A, the concept B, and the concept C; and
   outputting, from the hypothesis generation module, a hypothesis indicating an association among the concept A, the concept B, and the concept C, in response to the hypothesis generation module determining:
      that the concept A relates to the concept B;
      that the concept B relates to the concept C;
      that the concept A relates to the concept C; and
      that the semantic category associated with each of the concept A, the concept B and the concept C is the same type of semantic category.

5. A method of generating a hypothesis comprising:
   extracting concept A and concept C from a data set, wherein the extracting is performed by an entity extraction module specifically programmed to extract concepts from the data set;
   receiving the concept A and the concept C as inputs to a hypothesis generation module, wherein the hypothesis generation module is specifically programmed to generate a hypothesis;
   determining a concept A semantic category associated with the concept A;
   determining a concept C semantic category associated with the concept C; and
   outputting, from the hypothesis generation module, a hypothesis that the concept A is a substitute for the concept C, in response to the hypothesis generation module determining:
      that the concept A semantic category is the same semantic category as the concept C semantic category;
      that the concept A and the concept C are co-occurring throughout the data set; and that the concept A and the concept C have at least a predetermined quantity of commonly associated ancillary concepts.

6. A method of extracting semantic relationships among entities in a sentence, comprising:
   accessing at least one data set from a remote storage device specifically programmed to store data that represents documents containing at least one association between two or more entities;
   identifying a first sentence included in the at least one data set;
   extracting entities from the first sentence using an extraction engine specifically programmed to extract entities from a sentence;
   determining a semantic type associated with each of the entities;
   determining a relationship that exists between two or more of the entities;
   generating a subsequence that includes one or more semantic types and at least one verb, wherein the one or more semantic types include the semantic type associated with each of the two or more of the entities;
   calculating a weight value of the subsequence; and
   storing the subsequence, the weight value, the semantic type associated with each of the entities, and the relationship in a storage device that is specifically programmed to store the subsequence, the weight value, the semantic type associated with each of the entities, and the relationship.

7. The method of claim 6 further comprising:
   generating a Chi-Square score value for each of the one or more other subsequences and for the subsequence; and
   ordering the subsequence and the one or more other subsequences based on the Chi-Square score value of each of the subsequence and the one or more other subsequences.

8. The method of claim 7 further comprising:
   generating a hypothesis based on one or more subsequences that have higher Chi-Square score values relative to all of the one or more other subsequences and the subsequence.

9. The method of claim 6 further comprising:
   implementing token subsequence kernel algorithms using a processor specifically programmed to implement the token subsequence kernel algorithms.

10. The method of claim 6, wherein generating the subsequence comprises:
    limiting the one or more semantic types to less than five semantic types included in the subsequence.

11. The method of claim 6 further comprising:
    generating a part of speech tag associated with each of the entities.

12. The method of claim 6 further comprising:
    storing the weight value in a pattern-sentence matrix on a storage device comprising memory specifically programmed to store the pattern-sequence matrix.

13. A system that extracts semantic relationships among entities in a sentence, comprising:
    a communications module configured to communicate with a remote storage device configured to store data that represents documents containing at least one association between two or more entities, wherein the communications module facilitates the downloading of at least one data set from the remote storage device;
    a local storage device configured to store the at least one data set;
    an entity extraction module configured to:
       identify a first sentence included in the at least one data set; and
       extract entities from the first sentence; and
    a semantic relationship extraction module configured to:
       determine a semantic type associated with each of the entities;
       determine a relationship that exists between two or more of the entities;
       generate a subsequence that includes one or more semantic types and at least one verb, wherein the one or more semantic types include the semantic type associated with each of the two or more of the entities; and
       calculate a weight value for the subsequence; and
    the local storage device is configured to store the subsequence, the weight value, the semantic type associated with each of the entities, and the relationship.

14. The system of claim 13, wherein the semantic relationship extraction module is configured to:
    generate a Chi-Square score value for each of the one or more other subsequences and for the subsequence; and
    order the subsequence and the one or more other subsequences based on the Chi-Square score value of each of the subsequence and the one or more other subsequences.

15. The system of claim 14 further comprising a hypothesis generation module configured to generate a hypothesis based on one or more subsequences that have higher Chi-Square score values.

16. The system of claim 13 further comprising a processor configured to implement the token subsequence kernel algorithms.

17. The system of claim 13, wherein the semantic relationship extraction module is further configured to:
    limit the one or more semantic types to less than five semantic types included in the subsequence to generate the subsequence.

18. The system of claim 13, wherein the semantic relationship module is further configured to generate a part of speech tag associated with each of the entities.

19. The system of claim 13, wherein the local storage device is configured to store the weight value in a pattern-sentence matrix.

* * * * *